(12) United States Patent
Korshøj et al.

(10) Patent No.: US 12,409,263 B2
(45) Date of Patent: Sep. 9, 2025

(54) SYSTEM AND METHOD FOR ESTIMATION AND CONTROL OF COMPLIANCE AND PRESSURE/VOLUME VARIATIONS WITHIN A BODY CAVITY

(71) Applicant: Aarhus Universitet, Aarhus C (DK)

(72) Inventors: Anders Rosendal Korshøj, Risskov (DK); Peter Gorm Larsen, Hinnerup (DK); Peter Johansen, Risskov (DK); René Søndergaard Nilsson, Aarhus V (DK)

(73) Assignee: Aarhus Universitet, Aarhus C (DK)

( * ) Notice: Subject to any disclaimer, the term of this patent is extended or adjusted under 35 U.S.C. 154(b) by 1075 days.

(21) Appl. No.: 17/278,352

(22) PCT Filed: Sep. 25, 2019

(86) PCT No.: PCT/EP2019/075935
§ 371 (c)(1),
(2) Date: Mar. 22, 2021

(87) PCT Pub. No.: WO2020/064875
PCT Pub. Date: Apr. 2, 2020

(65) Prior Publication Data
US 2021/0369941 A1    Dec. 2, 2021

(30) Foreign Application Priority Data
Sep. 25, 2018   (EP) .................................... 18196550

(51) Int. Cl.
*A61M 1/00*      (2006.01)
*G16H 20/17*     (2018.01)

(52) U.S. Cl.
CPC ..... *A61M 1/777* (2021.05); *A61M 2205/3303* (2013.01); *A61M 2205/3334* (2013.01); *A61M 2210/0693* (2013.01); *G16H 20/17* (2018.01)

(58) Field of Classification Search
CPC ........ A61M 1/777; A61M 1/77; A61M 1/772; A61M 1/774; A61M 2205/3303;
(Continued)

(56) References Cited

U.S. PATENT DOCUMENTS

2005/0070458 A1    3/2005   John
2007/0249993 A1    10/2007  Mollstam et al.
(Continued)

FOREIGN PATENT DOCUMENTS

JP    2018517443 A    5/2018
RU      2494684 C1   10/2013
(Continued)

OTHER PUBLICATIONS

First Office Action for Russian Application No. 2021109119, dated Feb. 28, 2023.
(Continued)

*Primary Examiner* — Kami A Bosworth
*Assistant Examiner* — Avery Smale
(74) *Attorney, Agent, or Firm* — DINSMORE & SHOHL LLP

(57) ABSTRACT

Systems and methods are provided for controlled infusion, effusion, and/or perfusion of biological/biocompatible liquid to and from a body cavity of a subject, and for continuous control of body cavity parameters, for example in neuro-intensive care. Systems and methods may relate to estimating compliance and pressure/volume changes within a body cavity. A bio-liquid replacement system may include a sensor for continuously measuring at least one parameter associated with the cavity, a pump for infusing the liquid into and aspirating the liquid out of the cavity, a processing unit continuously calculating at least one physiological parameter based on the measured parameter, and defining a target parameter slightly offset from the physiological
(Continued)

parameter, and a flow controller controlling said pump unit based on the target parameter and the induced offset such that continuous compensatory changes are induced in the liquid volume. The processing unit continuously estimates the body cavity compliance.

26 Claims, 21 Drawing Sheets

(58) Field of Classification Search
CPC .. A61M 2205/3334; A61M 2210/0693; A61M 2230/30; A61M 2230/50; A61M 2202/0464; A61M 2205/3331; A61M 5/14; A61M 5/142; A61M 2005/14208; A61M 5/145; A61M 5/168; A61M 5/16804; A61M 5/16831; A61M 5/16836; A61M 5/16854; A61M 5/172; A61M 5/1723; A61M 2005/1726; G09B 23/30; G16H 20/17; G16H 40/63
See application file for complete search history.

(56) References Cited

U.S. PATENT DOCUMENTS

| | | | |
|---|---|---|---|
| 2010/0210958 A1 | 8/2010 | Manwaring et al. | |
| 2015/0254857 A1* | 9/2015 | Huang | G06T 7/33 382/154 |
| 2015/0290387 A1* | 10/2015 | Möllstam | A61M 3/0201 604/24 |
| 2017/0127946 A1 | 5/2017 | Levinson et al. | |
| 2020/0237977 A1* | 7/2020 | Panotopoulos | A61M 1/77 |

FOREIGN PATENT DOCUMENTS

| | | |
|---|---|---|
| WO | 2004/043313 A2 | 5/2004 |
| WO | 2006/091164 A1 | 8/2006 |
| WO | 2011/116393 A1 | 9/2011 |
| WO | 2015/109260 A1 | 7/2015 |
| WO | 2017096228 A1 | 6/2017 |

OTHER PUBLICATIONS

Japanese Office Action Notice of Reasons for Rejection dated Oct. 24, 2023, Application No. 2021-516408.
Ali S. et al. "A Proposed Management of Accidental Intrathecal Injection of a Wrong Drug: Spinal Washing". J.Appl. Environ.Biol. Sci 2014;4(8):292-295.
Aydin M. D. et al. "Protective effects of cisternal irrigation on leptomeningeal and cortical structures in meningitis: an experimental study". Neurol India Mar. 2005;53(1):90-92.
De Aguiar, Paulo H Pires et al. "Removal of clots in subarachnoid space could reduce the vasospasm after subarachnoid hemorrhage". Cerebral Vasospasm: Neurovascular Events After Subarachnoid Hemorrhage: Springer; 2013. p. 91-93.
Ding W. et al. "Clinical evaluation of the efficacy of the combination of aneurysm embolization and cerebrospinal fluid replacement in the treatment of aneurysmal subarachnoid hemorrhage". Eur Rev Med Pharmacol Sci 2015;19 (3):402-405.
Hannggi D. et al. "The influence of cisternal and ventricular lavage on cerebral vasospasm in patients suffering from subarachnoid hemorrhage: analysis of effectiveness. Early Brain Injury or Cerebral Vasospasm". Springer; 2011. p. 95-98.
Jakobson Å... et al. "Cerebrospinal fluid exchange after intrathecal methotrexate overdose. A report of two cases". Acta Paediatrica 1992;81(4):359-361.
Liu G et al: "Clinical observation of cerebrospinal fluid replacement combined with intrathecal injections in treatment of tuberculous meningitis". Chinese Journal of Nosocomiology 2011;13:044.
Makar G. et al. "Successful large-volume cerebrospinal fluid aspiration for an accidental overdose of intrathecal cytarabine". Medical Oncology 2013;30(2):1-3.
McBee N. et al. "Mortality Review For the First 400 Patients Enrolled in the Clot Lysis: Evaluation of Accelerated Resolution of Intraventricular Hemorrhage Trial (CLEAR III)". Stroke 2015;46(Suppl 1):A94.
Wyn, Guoqiang. Shaanxi Provincial T. "In 34 cases of tuberculous meningitis with cerebrospinal fluid replacement and intrathecal injection". Shaanxi Medical Journal 2013;6:039.

* cited by examiner

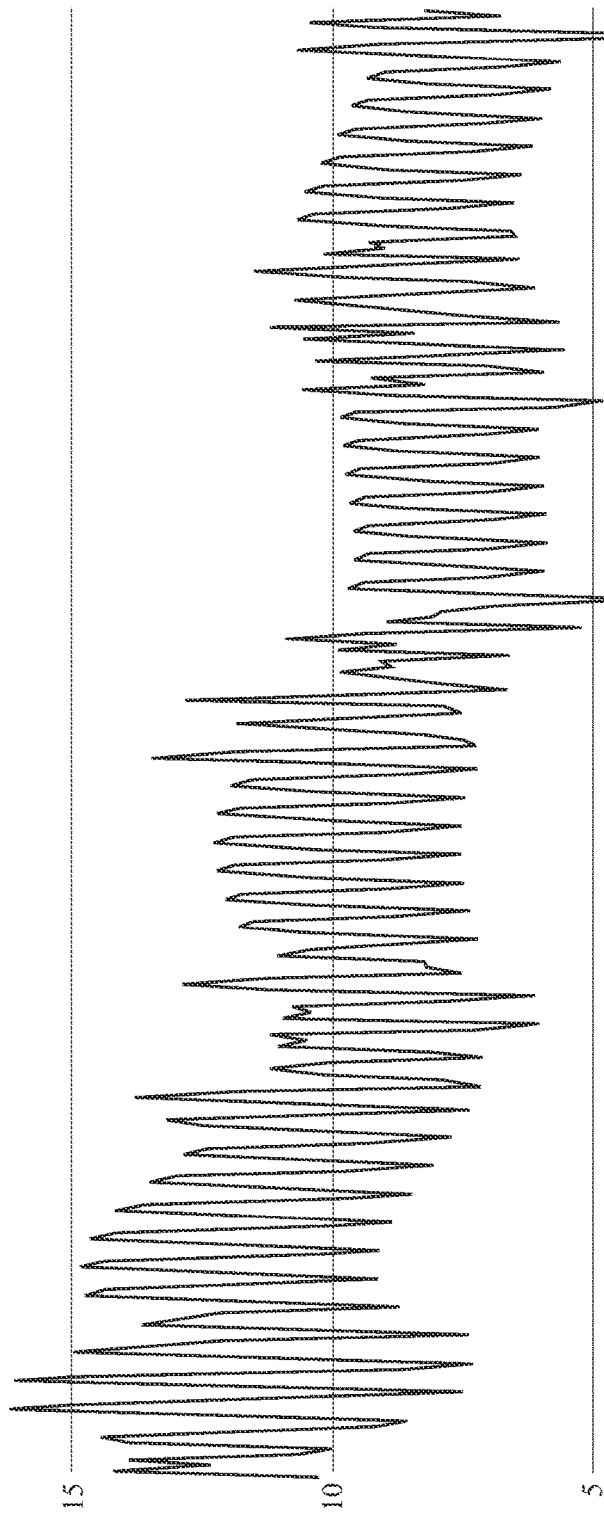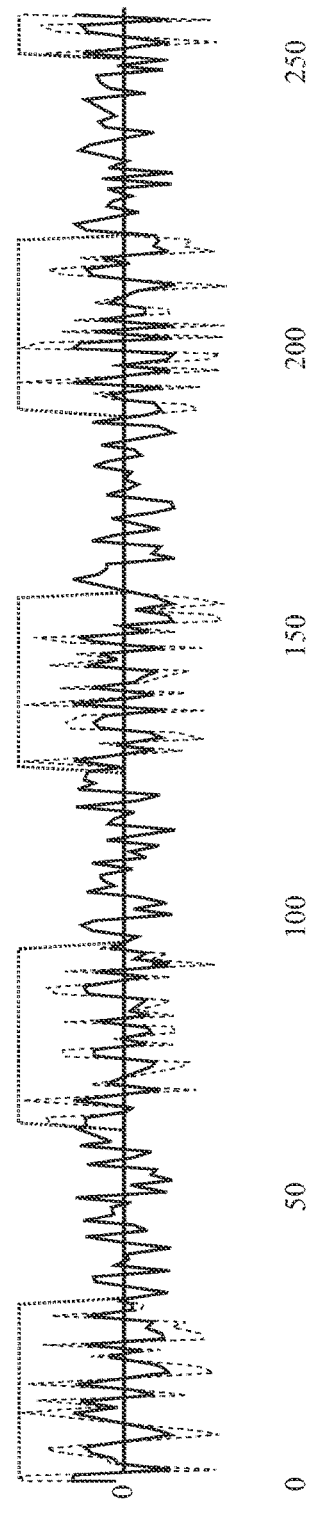
FIG. 15A
FIG. 15B

- - - - {C}.c.micp20
·········· {C}.c.pressureSetpoint_var
——— {P}.p.pressure
— — {P}.p.PressureSensor.MultiplyDivide.multiply1
——— {P}.p.PressureSensor.MultiplyDivide.multiply2
----- {P}.p.PressureSensor.MultiplyDivide.output

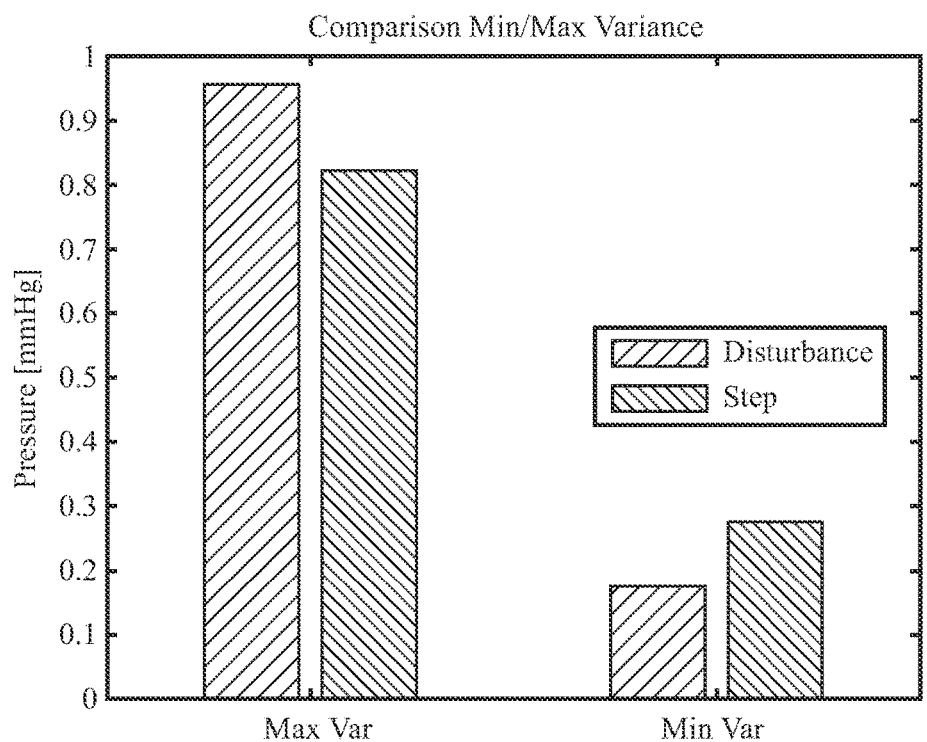
FIG. 25
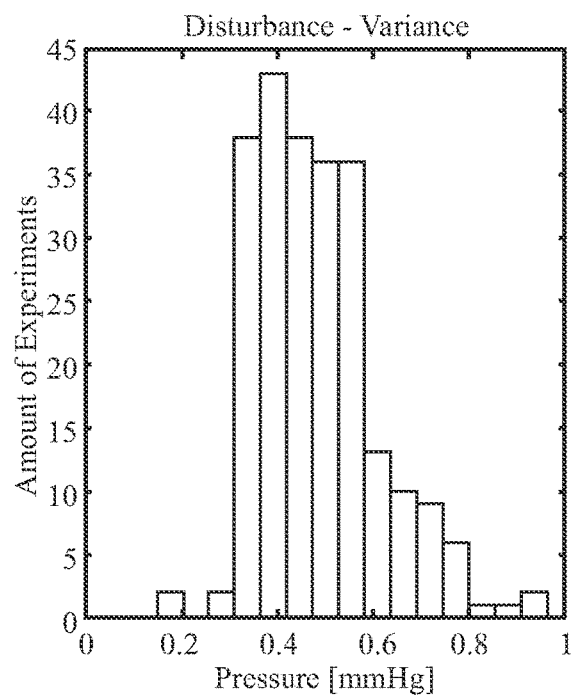 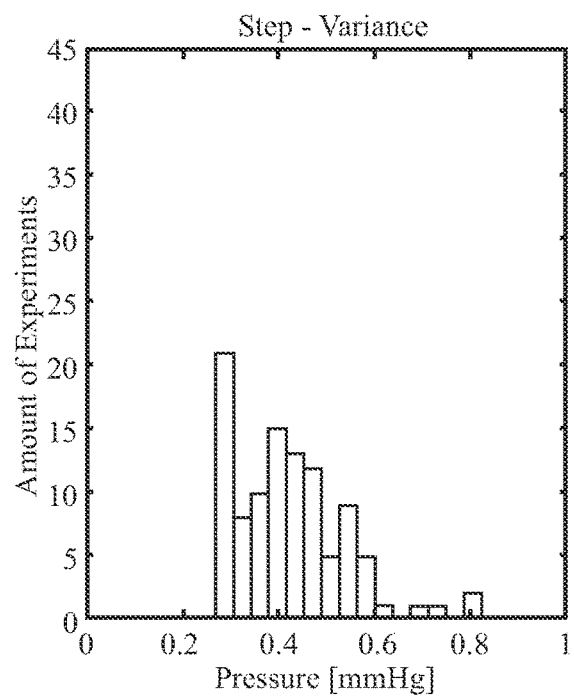
FIG. 26    FIG. 27

SYSTEM AND METHOD FOR ESTIMATION AND CONTROL OF COMPLIANCE AND PRESSURE/VOLUME VARIATIONS WITHIN A BODY CAVITY

CROSS REFERENCE TO RELATED APPLICATIONS

This application is the U.S. national stage of PCT/EP2019/075935 filed Sep. 25, 2019, which claims priority of European patent application 18196550.0 filed Sep. 25, 2018, both of which are hereby incorporated by reference in their entirety.

FIELD OF THE INVENTION

The present disclosure relates to systems and methods for controlled infusion, effusion, and/or perfusion of biological or biocompatible liquid to and from a body cavity of a subject, and for continuous control of the physical body cavity parameters, for example in relation to neuro-intensive care. In particular the present disclosure relates to systems and methods for estimating and/or controlling pressure/volume variations within a body cavity and systems and methods for estimating and/or controlling compliance within a body cavity.

BACKGROUND OF INVENTION

In USA there are 1.7 million traumatic brain injury (TBI) cases annually arising from mechanical trauma of which 80-90.000 people end up with long-term or lifelong disabilities. Direct medical costs and indirect costs (such as productivity losses) of TBI are estimated at $48-56 billion annually. The mortality rate for traumatic brain injury in US is 30/100.000 which is equivalent to 50.000 annual deaths in US. European statistical studies show likewise mortality rates of 9-28/100.000. Similarly, aggregate lifetime costs associated with one year's occurrence of intracerebral and subarachnoid hemorrhages in the US have been estimated to $12 billion. Direct admission costs amount to $23.000 per patient for subarachnoid hemorrhage and $10.300 for intracerebral hemorrhage and the corresponding mortality rates are approx. 30% for both conditions.

Neurotrauma is often associated with the presence of deleterious substances in the cerebrospinal fluid (CSF) surrounding the brain and the spinal cord. The CSF plays a vital role in maintaining homeostasis of the neuronal microenvironment. The presence of blood, infectious agents, cellular debris, or neurotoxins in the CSF, may result in life-threatening neuronal damage, cytotoxic brain edema, disruption of cerebral microcirculation, or obstruction of the natural outflow of the CSF. Removal of pathological substances therefore represents an important but challenging aspect of modern neuro-intensive care. Experimental treatment with CSF replacement and diversion has been shown to significantly improve the outcome of severe conditions, such as neuro-infections (1-3), subarachnoid hemorrhage, delayed cerebral ischemia, hydrocephalus (4-6), intra-ventricular hemorrhage (7), and intra-thecal drug over dosage (8-10). Techniques previously employed for such treatments include high-risk skull base surgery, and passive or manual CSF diversion. These techniques all pose considerable drawbacks with regard to efficacy or patient safety. Superior methods are therefore warranted.

In addition, neuro-trauma is associated with intracranial hypertension causing cerebral hypoxia and structural brain damage. Intracranial pressure control therefore represents an important element in neuro-intensive care. Conventional treatment includes sedation, intravenous infusion of hypertonic solutions, hyperventilation, and surgical treatment with passive external CSF drainage and controversial surgical craniectomy.

SUMMARY OF INVENTION

Despite extensive treatment the intracranial pressure often remains uncontrolled and technologies for accurate control are needed. Hence, there is a need for upgrading current technologies from labor-demanding and passive information providers to automated and controlled monitoring, i.e. active therapy that can accelerate neuro-intensive care and patient healing in order to improve clinical outcome with reduction of secondary disabilities after treatment.

Systems and methods are therefore needed, which enable continuous monitoring of each patient's intracranial pressure/volume relationship, since this indirectly reflects the reserve capacity for pathological intracranial volume expansion, e.g. due to bleeding, brain swelling or other mass lesions. This relationship can be suitably quantified by the so-called compliance measure, which is calculated as the slope of the pressure-volume curve at any time.

The purpose of the present disclosure is to advance and improve treatment of acute neuro-trauma. This can be achieved by 1) controlling the intracranial pressure in patients with pathological intracranial hypertension, 2) estimating and monitoring the intracranial compliance, pressure-volume relationship and the reserve capacity for intracranial volume expansion in neuro-trauma patients, and/or 3) performing safe and controlled perfusion/lavage of the subarachnoid space surrounding the brain and spinal cord in patients with the presence of pathological, toxic or obstructive substances in the subarachnoid space or with a need for continuous direct application of medical drugs in the cerebrospinal fluid.

The present disclosure therefore in a first aspect relates to a bio-liquid replacement system for controlled infusion, effusion, and/or perfusion of biological or biocompatible liquid to and from a body cavity, such as the intracranial volume. The bio-liquid replacement and pressure control system comprises at least one sensor for continuously measuring at least one parameter associated with the body cavity. A (physical) parameter representing for example the intracranial pressure (ICP), which can be measured by a sensor inside the body cavity, or a parameter like the liquid flow rate (to and/or from the body cavity), which can be measured outside the body cavity. A pump unit, comprising one or more pumps, can be provided for infusing the liquid into the body cavity and aspirating the liquid out of the body cavity. A processor/processing unit can be provided which is configured for continuously 1) calculating at least one physiological parameter based on the at least one measured or estimated parameter, and 2) defining at least one target parameter. The purpose of the target parameter is to define a desired value for the physiological parameter. The target parameter provides a control parameter for the system/method, such that it will attempt to correct any offset between the physiological parameter and the target parameter. The processing unit, typically comprising a processor and memory, e.g. part of a general purpose computer or any type of processing device, is configured to calculate a physiological parameter based on the measured parameter. The processing unit also determines a target parameter, typically based on user input and system configurations, and typically based on the physiological parameter. The target parameter may be defined such that an offset is provided between the physiological parameter and the target parameter. In such scenarios, the system is preferably configured with a time-varying target signal, which creates continuous time-varying offset, which thereby can be used to introduce a controlled time variation of the system parameters including the physiological parameter. I.e. the present invention may be at least partly computer implemented.

A flow controller can be provided which is configured for controlling the pump unit based on said at least one target parameter. A time varying offset between the physiological parameter and the target parameter, can then have the effect that continuous compensatory changes are induced in the system, e.g. continuous compensatory changes, typically very small changes, in the liquid volume in the body cavity. Once a time variation is introduced by the system, compliance inside the body cavity can be estimated, based on the induced changes in body cavity pressure and volume. I.e. the physiological parameter that is continuously calculated and its offset relative to the target parameter will reflect this time variation and hence the processing unit may be configured for continuously estimating the compliance within the body cavity based on variations in said at least one calculated physiological parameter, which can reflect variations in for example the body cavity pressure, the liquid flow rate, and/or volume changes within the body cavity. I.e. with the presently disclosed system a feedback regulation of intracranial fluid infusion and/or aspiration and/or perfusion is provided. I.e. control of pressure/volume variations within a body cavity is provided by the present disclosure.

The time variation due to the offset that is induced by the presently disclosed system are required to ensure continuous estimation of the body cavity compliance and the system may therefore appropriately employ or induce such variations to ensure that compliance is well-defined and possible to estimate. Variations in for example the calculated body cavity pressure and liquid flow rates (volume changes) may be ensured by imposing time-variations in a target parameter, such as the body cavity target pressure. This will induce a minor continuous off-set between the body cavity target parameter (e.g. target pressure) and the calculated parameter, which is based on a measured parameter. If it is the body cavity pressure, it can be the measured parameter that is used directly as the calculated parameter, but the calculated parameter can also be e.g. a functional modification of the measured body cavity pressure, such as a moving average of the body cavity pressure, and/or a functional modification of the measured or estimated volume changes in the body cavity.

This minor offset between measured or estimated body cavity pressure, or functional modification thereof, and the time-varying target pressure, will cause the flow controller to induce continuous compensatory volume changes in the body cavity, thereby enabling regular and preferably continuous estimation of the body cavity compliance. Alternatively the target parameter can be a constant time-invariant signal, e.g. a constant ICP target. The corresponding measured parameter (process variable) can then be the measured ICP or a functional modification of the ICP. In this case the time varying offset between the physiological parameter and the target parameter will come from natural time variations in the ICP signal. The control algorithm will then try to counteract these natural time-variations in the ICP signal, by performing correctional volume changes, e.g. corresponding approximately to the volume changes caused by changes in the intra-cranial blood-volume as a result of the heartbeat, or other physiological intracranial volume changes. This will enable repeated or continuous compliance estimation, while attempting to maintain a near-constant ICP and intracranial volume. Also, it will enable continuous estimation of the time-variations in the physiological intracranial parameters, such as the physiological volume changes.

The notion of introducing an offset between the physiological parameter and the target parameter, such that a time-variation is induced in the system, is a key aspect of the present invention, because the controlled variation is a body cavity parameter that allows for continuous estimation of the body cavity compliance. The time-variations in body cavity target parameters (e.g. body cavity target pressure) may be based on naturally varying physiological signals, such as continuous arterial blood pressure signals or variations originating from breathing of the subject, or predefined non-physiological time-varying signals, such as a sine-wave signal.

A further embodiment relates to a compliance estimator system for estimating compliance within a body cavity, comprising
 a communication unit for receiving data corresponding to at least one measured parameter related to the body cavity and for communicating with a flow controller, and
 a processor configured for
  a) calculating at least one physiological parameter based on the at least one measured parameter,
  b) defining at least one target parameter such that the target parameter is slightly offset from the physiological parameter, preferably in a time varying manner,
  c) forwarding a control signal, based on at least one target parameter, to the flow controller, such that continuous compensatory changes are induced in the liquid volume in the body cavity,
  d) repeating steps a)-c)
  wherein the compliance within the body cavity is continuously estimated based on said at least one calculated physiological parameter.

The communication unit may be configured for receiving data corresponding to the infusion rate, the effusion rate and/or the perfusion rate of a biological or biocompatible liquid to and from the body cavity.

The present disclosure further relates to method for estimating compliance within a body cavity of a subject based on controlled infusion, effusion, and/or perfusion of biological or biocompatible liquid to and from the body cavity, the method comprising the steps of:
 continuously obtaining at least one physiological parameter associated with the body cavity,
 continuously defining at least one target parameter associated with the body cavity, such that the target parameter is slightly offset from the physiological parameter, preferably in a time varying manner, such that continuous compensatory changes are induced in the liquid volume in the body cavity, and
 continuously estimating compliance within the cavity based on said at least one physiological parameter.

I.e. in other words it can be said that in the presently disclosed approach the measured and estimated parameters are used to produce an estimate of the body cavity pressure-volume relationship, for example a system wherein the measured pressure and the inverse of the estimated compliance at corresponding time-points are used to represent the independent variable and the slope of the intracranial pressure-volume relationship at the given time-point, respectively. I.e. the measured and estimated parameters may be used to produce an estimate of the body cavity reserve-volume capacity, preferably a system wherein the estimated intracranial compliance and the estimated intracranial pressure-volume relationship is used to estimate the change in the intracranial volume, such that an intracranial pressure attaining a given value is obtained, such as a critical threshold value.

The systems and methods presented herein can enable both automated and continuous pressure control, compliance measurement and CSF perfusion thereby addressing all the stated needs.

The present disclosure allows for optimized care and monitoring of neuro-trauma patients and addresses significant clinical challenges associated with a wide range of severe and debilitating neurological diseases. The present disclosure provides valuable predictive measures of brain function in addition to direct and controlled therapeutic actions. The technology may be applied with the sole objective to control intracranial pressure using minimal CSF exchange, but also in cases where pressure control, compliance measurement and CSF replacement are all indicated. Examples of applications are for treatment of intracranial hematoma, subdural hematoma, acute subdural hematoma, chronic subdural hematoma, subdural hygroma, subdural empyema, and/or subdural abscess, see for example FIG. 32 Automated and feedback regulated therapy can be provided based on direct monitoring of prognostic measures, which is highly valuable for both patients and caregivers. It provides easier and more sophisticated patient monitoring as well as effective therapeutic pressure control. In addition, the present disclosure presents a solution for subarachnoid lavage, which potentially has great therapeutic impact. The presently disclosed approach will expectedly result in better patient outcome, reduced time of admission and reduced costs of rehabilitation.

Hence, the present disclosure further relates systems and methods for controlled infusion, effusion, and/or perfusion of biological or biocompatible liquid to and from a body cavity of a subject, and/or for continuous control of the physical body cavity parameters, for treatment of any of the diseases and/or conditions selected from the group of intracranial hematoma, subdural hematoma, acute subdural hematoma, chronic subdural hematoma, subdural hygroma, subdural empyema, and subdural abscess, wherein the presently disclosed system and/or method can be used for estimating the compliance of the corresponding body cavity for resulting therapeutic pressure control. See for example FIG. 32. The drainage tube is typically located in the accumulated bodily fluid. Thereby, if necessary, performing safe and controlled perfusion/lavage of the corresponding body cavity, e.g. with the presence of pathological, toxic or obstructive substances in the subarachnoid space or with a need for continuous direct application of medical drugs in the bodily fluid.

DESCRIPTION OF DRAWINGS

In FIG. 12 the pressure setpoint was 5 mmHg, in FIG. 13 the pressure setpoint was 10 mmHg, and in FIG. 14 the pressure setpoint was 15 mmHg.

FIGS. 15A-B show how noise added to the pressure affects a disturbance test; noise was added to simulate a noisy pressure sensor.

FIGS. 22-31 show various result overviews from 103 step test simulations and 237 disturbance test simulations.

DETAILED DESCRIPTION OF THE INVENTION

Figure 1:
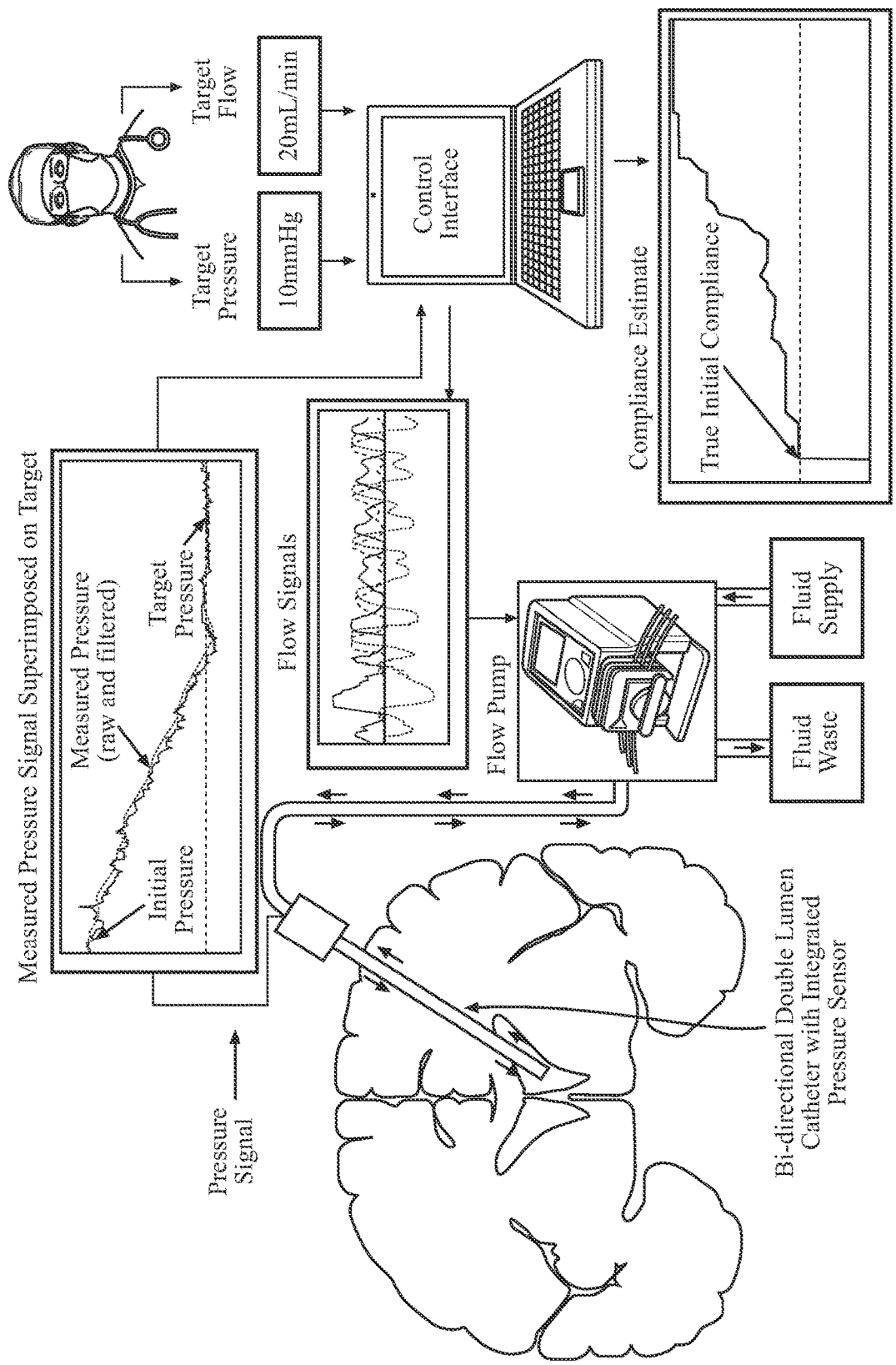
FIG. 1 illustrates an example of the physical setup for the presently disclosed bio-liquid replacement system. A flow pump controls the infusion and aspiration of CSF fluid, while a pressure sensor in a double lumen catheter provides feedback to the control algorithm, which controls the pump via serial communication. Inputs in terms of settings, such as pressure and flow rate targets, can be set through the control interface on the computer providing a compliance estimate.

The actual body cavity as used herein may be located inside the intracranial space or spinal canal of a human or animal.

A measured parameter associated with the body cavity is a parameter that can be directly measured, e.g. a pressure sensor can measure pressure, e.g. inside the body cavity, liquid flow rate can also be measured directly. A measured parameter may also be referred to as a process parameter.

A calculated physiological parameter can be similar to the measured parameter or it can be a functional modification of the measured parameter, e.g. a moving average of the measured parameter or calculation of associated volume change based on measured flow rate. The calculated physiological parameter is a process parameter, which the presently system will attempt to control by means of feedback mechanisms.

A (body cavity) target parameter typically defines a desired setpoint value for a corresponding calculated physiological parameter. The target parameter may vary in time and thereby define a target parameter signal, defining the desired time-variations of the corresponding physiological parameter. In one embodiment, the target parameter may the desired value of the body cavity pressure at a given point in time.

An error signal defines the offset (error) between the physiological parameter value and the target parameter value. It is a function of the physiological parameter and the target parameter. The error signal may define the difference between the calculated physiological parameter value at time t and the corresponding target parameter value at time t.

A control signal defines a signal of the presently disclosed system to regulate the system output, e.g. the control output to the flow controller. The control signal may be based on the error signal or a mathematical modification of the error signal. The control signal can be used as an input to a control algorithm that can be provided to regulate the system output.

A system output signal can be seen as a regulatory signal, e.g. an output from the control algorithm. In one embodiment, the system output signal is configured to cause modifications of a physiological body cavity parameter in an attempt to minimize the error signal. The system output signal can for example be an input to the flow controller in the form of a specific the liquid infusion rate and/or liquid effusion rate and/or perfusion rate which is changed in order to regulate the liquid volume of the body cavity.

The measured parameter is typically the intra-cranial pressure. However, the presently disclosed approach can also apply to other physical parameters, which can be selected from the group of: pressure, temperature, oxygen tension, liquid flow rate, and concentration of at least one predefined biological compound.

The measured parameter(s) may be functionally modified to provide the calculated physiological parameter, e.g. estimated as a function, $f$, of at least one measured physical parameter, such as a moving average, which is an average acquired over a predefined period of at least one digital sampling period, or at least one millisecond, or at least 1 second, or at least 3 seconds, or at least 5 seconds, or at least 10 seconds, or at least 20 seconds. Such modified process parameters may potentially be used to improve stability of the presently disclosed approach of applying small variations in order to estimate compliance, because a moving average can ensure that unwanted correction of variations are avoided, e.g. due to as natural variations in the body cavity pressure.

The target parameter may be selected from the group of: target pressure, target temperature, target oxygen tension, target liquid flow rate, and target concentration of at least one biological compound. Selection of the body cavity target parameter can be defined externally, such as by a user of the method or system. The body cavity target parameter(s) will typically correspond to body cavity process parameter.

The system output is typically the body cavity liquid infusion rate and/or the body cavity liquid effusion rate and/or the body cavity liquid perfusion rate. The system output signal will typically attempt to minimize the error signal that results from the offset between the target parameter and the process parameter. At least one predefined external signal may be applied to the regulatory system output signal. The external signal(s) may be a constant time-invariant signal defining the desired baseline body cavity liquid perfusion rate and/or baseline body cavity liquid infusion rate and/or baseline body cavity liquid effusion rate. In that case the system will perform body cavity liquid perfusion at a predefined baseline flow rate, while simultaneously controlling at least one additional process parameter, such as the body cavity pressure.

The biological liquid as used herein may be cerebrospinal fluid or modified cerebrospinal fluid. Similarly the biocompatible liquid may be artificial cerebrospinal fluid, modified artificial cerebrospinal fluid, or other physiological solutions and/or solutions containing medical drugs.

A key aspect of the present invention is the realization that compliance can be estimated within the body cavity by utilizing a timely modification of the body cavity target parameter. This modification can be provided externally, for example by a predefined non-physiological time-varying signal. In one embodiment the predefined modification of the target parameter is defined as a time-varying function, such as a sine wave or a piecewise constant function (step-function), for example having a predefined amplitude and/or period. The time varying function may be defined by means of an amplitude and/or a frequency. Amplitudes can be in the range of between 0.01 and 3 mmHg, such as between 0.1 and 2 mmHG, preferably between 0.3 and 1 mmHg. The frequency will typically be rather low, possibly less than 0.5 Hz, preferably less than 0.2 Hz, more preferably less than 0.1 Hz, even more preferably less than 0.05 Hz, most preferably less than 0.02 Hz, for example around 0.01 Hz or even lower. A frequency of 0.01 Hz provides a period of the time varying function of around 100 seconds.

In another embodiment the time-varying target parameter signal is a physiological signal, e.g. a signal originating from the heartbeat and/or breathing of the patient.

In one embodiment, the system uses at least one physical access pathway to the body cavity to perform liquid infusion, effusion or perfusion continuously or sequentially. In another embodiment, the system uses multiple access pathways to the body cavity to perform said liquid infusion, effusion, or perfusion continuously or sequentially and the direction of flow infusion and/or effusion and/or perfusion may be changed in each access pathway to allow for directional flow changes and prevention of access pathway obstruction. Flow direction control will be performed by the flow controller and the associated pump unit, which comprises one or more pumps.

Compliance Estimation

Compliance is defined as dV/dP, where V is volume and P is pressure, and d defines the differential operator or difference operator of a variable over time. In theory this is straight forward to calculate, if volume flow and pressure can be estimated. However, in reality estimation of volume flow is only partially possible. The external volume flow that the pump produces can be controlled, but any internal CSF production/absorption or other physiological volume flows are not directly measurable. Intracranial pressure (ICP) can also be controlled, but it cannot be known for sure that changes in ICP are caused exclusively by intracranial volume changes caused by external flow variations. Additionally, the heartbeat causes rapid fluctuations in ICP, however, because the intracranial volume change associated with each heartbeat is unknown, it is not possible to directly measure the intracranial compliance based on these fluctuations alone. Therefore, it is currently necessary to induce controlled intracranial volume changes in order to estimate the intracranial compliance.

The compliance, $\hat{c}_{raw}(t)$, at time t can be estimated as $$\hat{c}_{raw}(t) = \frac{\int_{t_s(t)}^{t} \Delta\dot{v}(k)dk}{f_p(t) - f_p(t_s)},$$

where $\Delta\dot{v}(k) = \dot{v}_{infusion}(k) - \dot{v}_{aspiration}(k)$ is the net perfusion flow rate at time k in the interval $[t_s, t]$, $\dot{v}_{infusion}(k)$ in the infusion flow rate at time k in the interval $[t_s, t]$, $\dot{v}_{aspiration}(k)$ the aspiration flow rate at time k in the interval $[t_s, t]$, and $f_p(t)$ the value of a function, $f$, on the measured pressure, p, at time t. This can be seen as the unfiltered (raw) estimate of the compliance. $\int_{t_s(t)}^{t}\Delta\dot{v}(k)dk$ estimates the total intracranial volume change in the time interval $[t_s, t]$ and $f_p(t) - f_p(t_s)$ estimates the total pressure change in the same time interval. I.e. the expression is a linear approximation of dV/dP from time $t_s(t)$ to t, where $t_s$ can be defined as $$t_s(t) = \begin{cases} t, & \text{if } \text{sign}(\Delta\dot{v}(t)) \neq \text{sign}(\Delta\dot{v}(t - \delta t)) \\ t - T_{limit}, & \text{if } \text{sign}(\Delta\dot{v}(t)) = \text{sign}(\Delta\dot{v}(t - \delta t)) \text{ and } t - t_s(t - \delta t) \geq T_{limit} \\ t_s(t - \delta t), & \text{if } \text{sign}(\Delta\dot{v}(t)) = \text{sign}(\Delta\dot{v}(t - \delta t)) \text{ and } t - t_s(t - \delta t) < T_{limit} \end{cases}$$

The first line in this definition defines a reset situation: sign( . . . ) is the sign function. If the sign of $\Delta\dot{v}(t)$ changes within a small time-window t−δt, i.e. the perfusion changes from net infusion to net aspiration, then the estimation calculation is 'reset', meaning that all old values are discarded, i.e. the compliance estimation is reset if the sign of the net flowrate changes.

The second line defines a time window of width $T_{limit}$, wherein compliance is estimated, i.e. a maximum number of samples is used for estimating compliance. Since the estimation is a linear approximation of an exponential function, a time limit is set on how long time the approximation should span.

The third line defines a situation with less samples, e.g. after a reset. In such a situation only the available samples are used until the width of the time window, defined in the second line, is reached.

In a further embodiment $t_s(t)$ is discretised as $$i_s[i] = \begin{cases} i, & \text{if } \text{sign}(\Delta\dot{v}[i]) \neq \text{sign}(\Delta\dot{v}[i-1]) \\ i - \frac{T_{limit}}{T_{sample}}, & \begin{array}{l}\text{if } \text{sign}(\Delta\dot{v}[i]) = \text{sign}(\Delta\dot{v}[i-1]) \text{ and} \\ i - i_s[i-1] \geq \frac{T_{limit}}{T_{sample}}\end{array} \\ i_s[i-1], & \begin{array}{l}\text{if } \text{sign}(\Delta\dot{v}[i]) = \text{sign}(\Delta\dot{v}[i-1]) \text{ and} \\ i - i_s[i-1] < \frac{T_{limit}}{T_{sample}}\end{array} \end{cases}$$

where $T_{sample}$ is the sampling time and $T_{limit}$ is a predefined period of time. Alternatively the compliance can be estimated as $$\hat{c}_{raw}[i] = \frac{\sum_{k=i_s}^{i} \Delta\dot{v}[k]}{f_p[i] - f_p[i_s]}.$$

This is equivalent to the definition above but with discrete signals.

A moving average ($mICP_x$) of the ICP over a predefined period of time y is preferably used as the function $f$, for example a 5 second moving average ($mICP_5$), rather than the ICP directly. This is performed in order to ensure that compliance estimation is based only changes in externally induced, i.e. controlled, volume and pressure changes, and not fluctuations in ICP caused by the heartbeat by volume changes, which cannot be estimated. For example, in the case where an external non-physiological time-varying signal is used as the desired target parameter signal, it can be necessary to filter or average out natural variations of the measured/monitored parameter, e.g. caused by the heartbeat of the patient.

In a further embodiment, the target parameter is a constant time-invariant signal, e.g. a constant ICP target. The corresponding measure parameter (process variable) can then be the measured ICP or a functional modification of the ICP. In this case the time varying offset between the physiological parameter and the target parameter will come from natural time variations in the ICP signal. The control algorithm will then try to counteract these natural time-variations in the ICP signal, by performing correctional volume changes, e.g. corresponding approximately to the volume changes caused by changes in the intra-cranial blood-volume as a result of the heartbeat, or other physiological intracranial volume changes. This will enable repeated or continuous compliance estimation, while attempting to maintain a near-constant ICP and intracranial volume.

In a further embodiment, a physiological time-varying signal, such as the measured/monitored arterial blood-pressure time signal, or the measured/monitored ICP, or modifications of said signals, may be used to define the target parameter signal.

The compliance estimate may further be calculated based on modifications of $\int_{t_s(t)}^{t} g(\Delta\dot{v}(k))dk$ and $f_p(t) - f_p(t_s(t))$, preferably such that tolerance limits are defined for $\int_{t_s(t)}^{t} g(\Delta\dot{v}(k))dk$ and $f_p(t) - f_p(t_s(t))$, preferably where a lower tolerance limit is defined for $f_p(t) - f_p(t_s(t))$.

Outliers can furthermore be removed in the compliance estimation. The compliance estimation can also be filtered, such as low-pass filtered, e.g. in accordance with $$\hat{c}(t) = \begin{cases} \alpha \cdot \hat{c}_{raw}(t) + (1 - \alpha) \cdot \hat{c}_{raw}(t-1), \\ \text{if } \hat{c}_{raw}(t) > 0 \text{ and } \text{var}(\hat{c}_{raw}(t_s, \ldots, t)) < VarLimit \\ \hat{c}(t-1), \text{ otherwise} \end{cases}$$

Where $\alpha$ is a filter coefficient and var( . . . ) is the variance function and is a predefined variance limit.

The estimated compliance or pressure-volume relationship may be represented in a variety of ways. In one embodiment, the compliance is represented as a time-varying signal, as explained above. In a further embodiment, the compliance is represented by at least one selected point on the time-varying signal, or a functional modification of at least one selected point on the time-varying signal, e.g. the estimated compliance could be obtained by selecting compliance estimates for local time-points at which the time-varying compliance signal has converged to a stable value, where stable refers to low variance of the compliance estimate. In a further embodiment, the compliance is represented along with the corresponding pressure- or volume estimate. This is relevant because the pressure volume-curve of a subject is expectedly monotonic and continuously differentiable, such that its equivalent relationship may be represented by the corresponding pressure-compliance relationship. This representation may be produced at different absolute pressure values within a particular time range and the estimation may be functionally modified and repeated over time.

The sensor may be an implantable sensor, such as an implantable pressure sensor. Alternatively the sensor may be a non-invasive sensor, such as a non-invasive pressure sensor. At least one flow sensor can furthermore be provided for measuring the infusion rate, the effusion rate and/or the perfusion rate.

The presently disclosed system may include one or more catheters for transporting the liquid into and out of the body cavity, such as one or more dual lumen catheters. The pressure sensor can then be integrated into one of the catheters and thereby be transported into the body cavity of the patient. Alternatively the pressure sensor can be located outside the body cavity and even outside the patient and configured to sense the body cavity pressure therefrom, for example via a fluid column.

EXAMPLES

Figure 2:
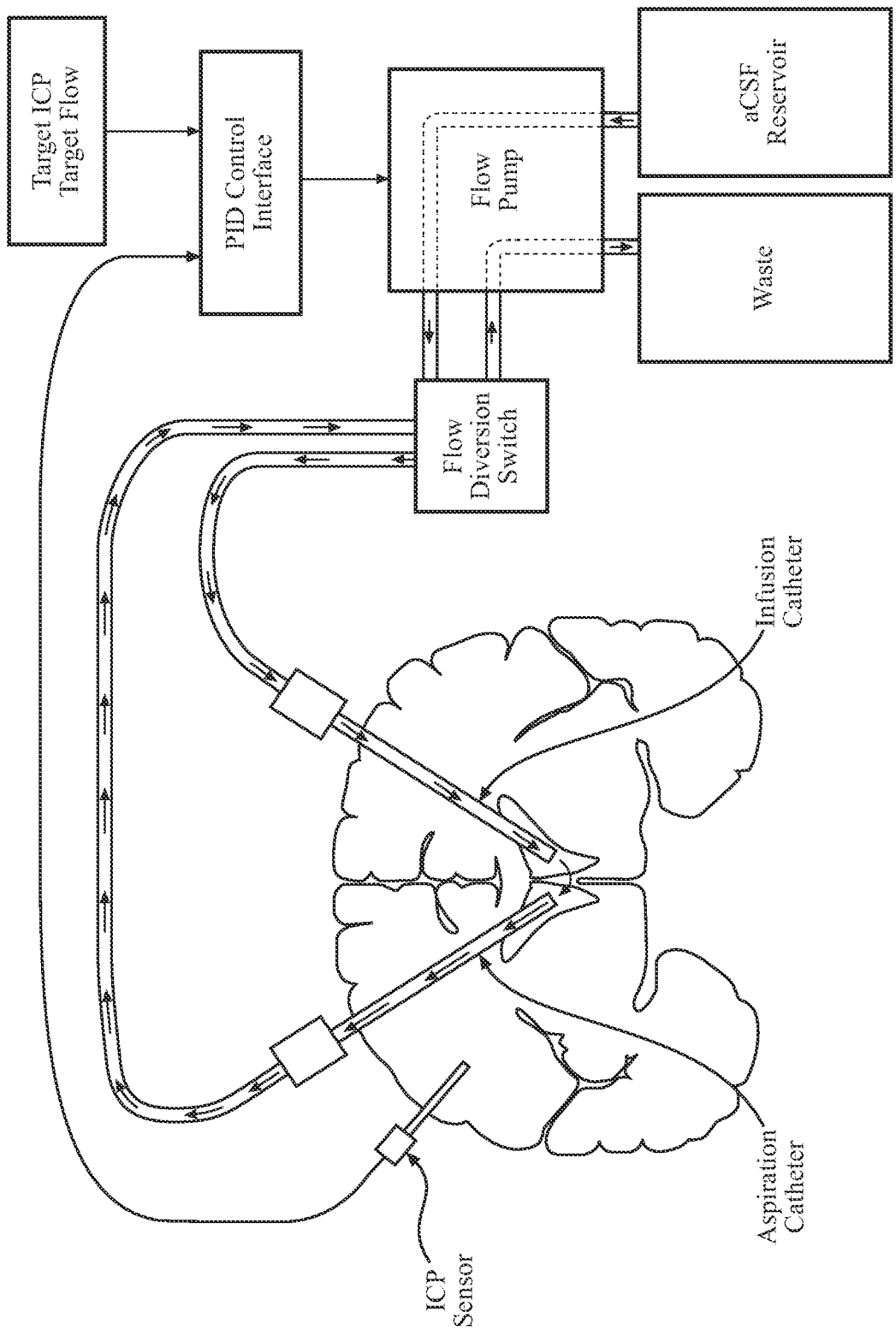
FIG. 2 shows an outline of one embodiment of the presently disclosed bio-liquid replacement system.

FIGS. 1 and 2 show illustrative outlines of embodiments of the presently disclosed bio-liquid replacement system. FIG. 2 shows a coronal section of a brain with insertion of one flow catheter into the lateral ventricle of either brain hemisphere. Each catheter is connected to a flow diversion switch via standard calibre tubing. The flow diversion switch determines which catheter is used for infusion and which is used for aspiration. Flow is produced by a flow-pump connected to the flow diversion switch. Artificial CSF for infusion is provided by a closed reservoir, such as 1 L or 2 L bag. Fluid aspired from the CSF space is deposited into a closed waste bag. Infusion and aspiration flow rates are controlled by a PID control interface. The control algorithm uses externally defined baseline values for average CSF exchange flow rate (perfusion flow rate) and furthermore adjusts the net perfusion flow rate to obtain a desired intracranial pressure. The baseline flow rate and target pressure values are provided directly by the user/clinician. Feedback pressure information is provided to the control algorithm by a standard pressure sensor.

Figure 4:
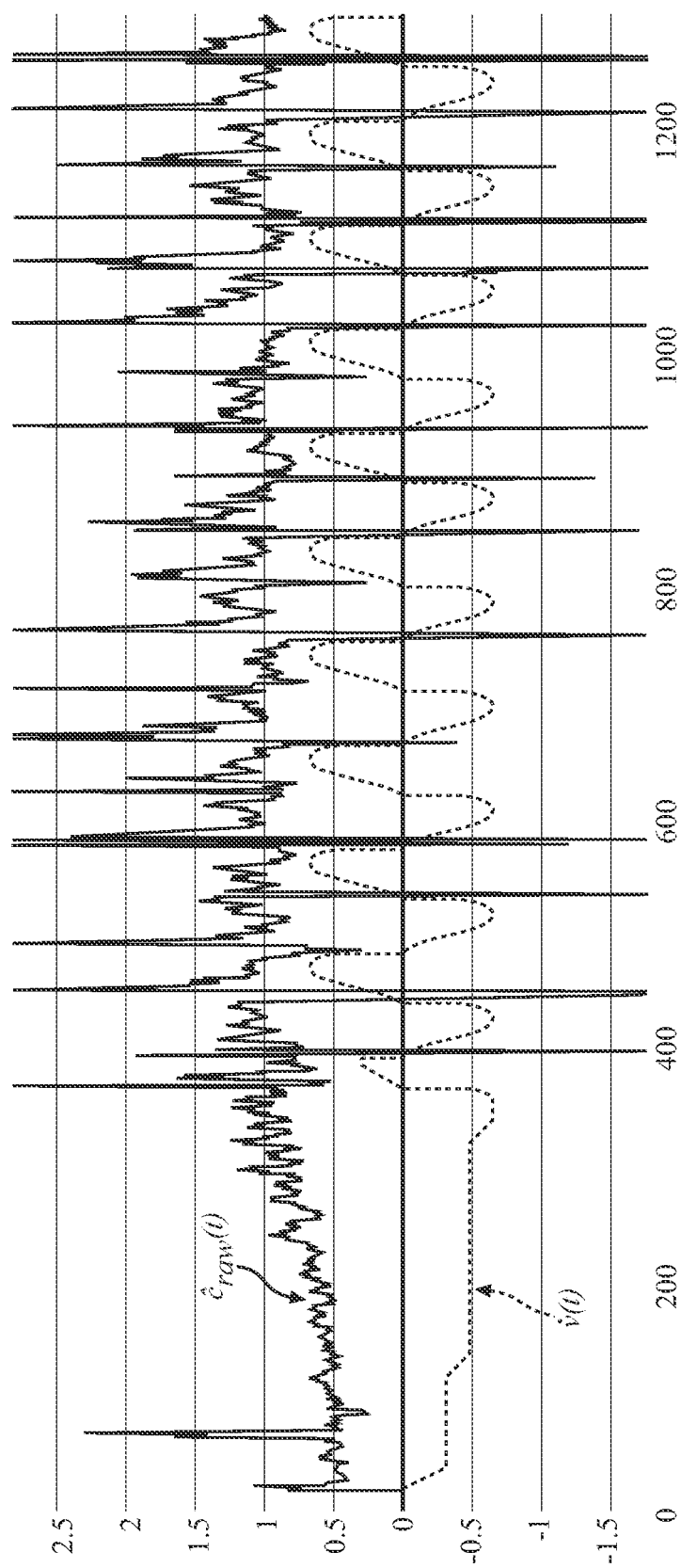
FIG. 4 shows the estimated compliance unfiltered $ĉ_{raw}(t)$ plotted together with the total estimated volume change $\dot{v}(t)$ for a given simulation scenario.
Figure 5:
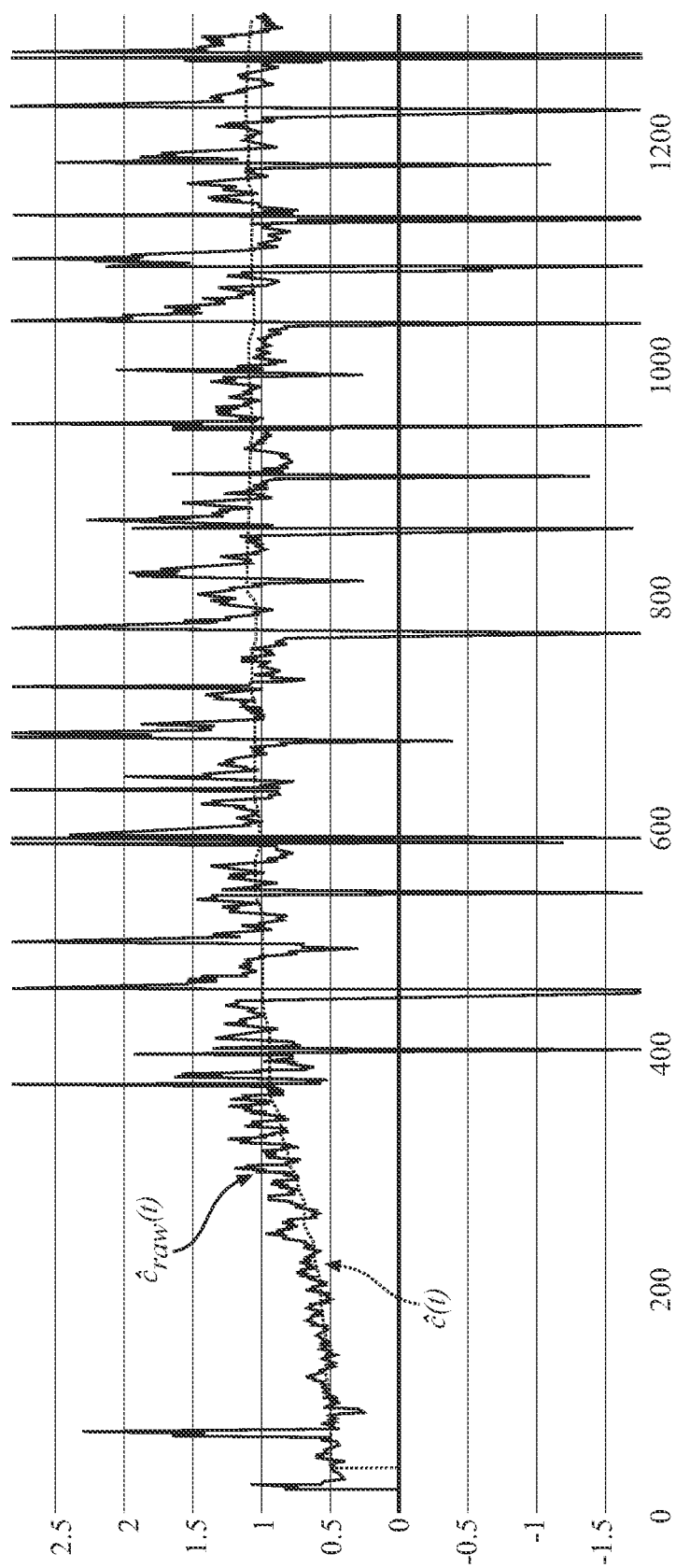
FIG. 5 shows estimated compliance unfiltered $ĉ_{raw}(t)$ and filtered $ĉ(t)$.

In FIG. 4 $ĉ_{raw}(t)$ (i.e. unfiltered) is plotted together with $\dot{v}(t)$ for a given simulation scenario. The unfiltered estimated compliance $ĉ_{raw}(t)$ is very fluctuating, especially after every reset of the calculation where $t_s=t=\int_{t_s}^{t}\Delta\dot{v}(t)dt=0$ $t_s=t=\int_{t_s}^{t}\Delta\dot{v}(k)dk=0$. To give a valid estimate of the compliance $ĉ(t)$, outliers are removed from $ĉ_{raw}(t)$, which is subsequently low pass filtered as described previously. FIG. 5 shows $ĉ_{raw}(t)$ and $ĉ(t)$, whereas FIG. 6 shows $ĉ(t)$ and the real simulated compliance.

Figure 6:
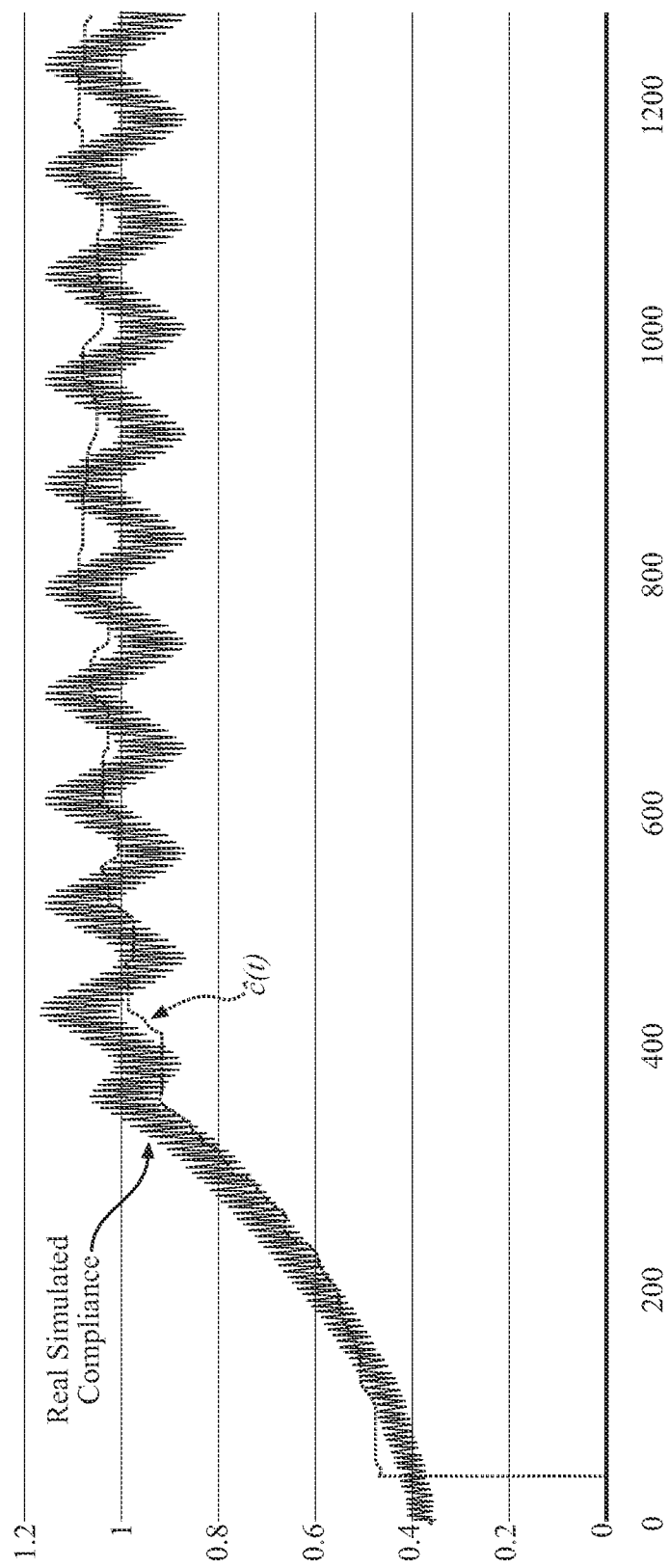
FIG. 6 shows estimated compliance $ĉ(t)$ and true compliance.
Figure 7:
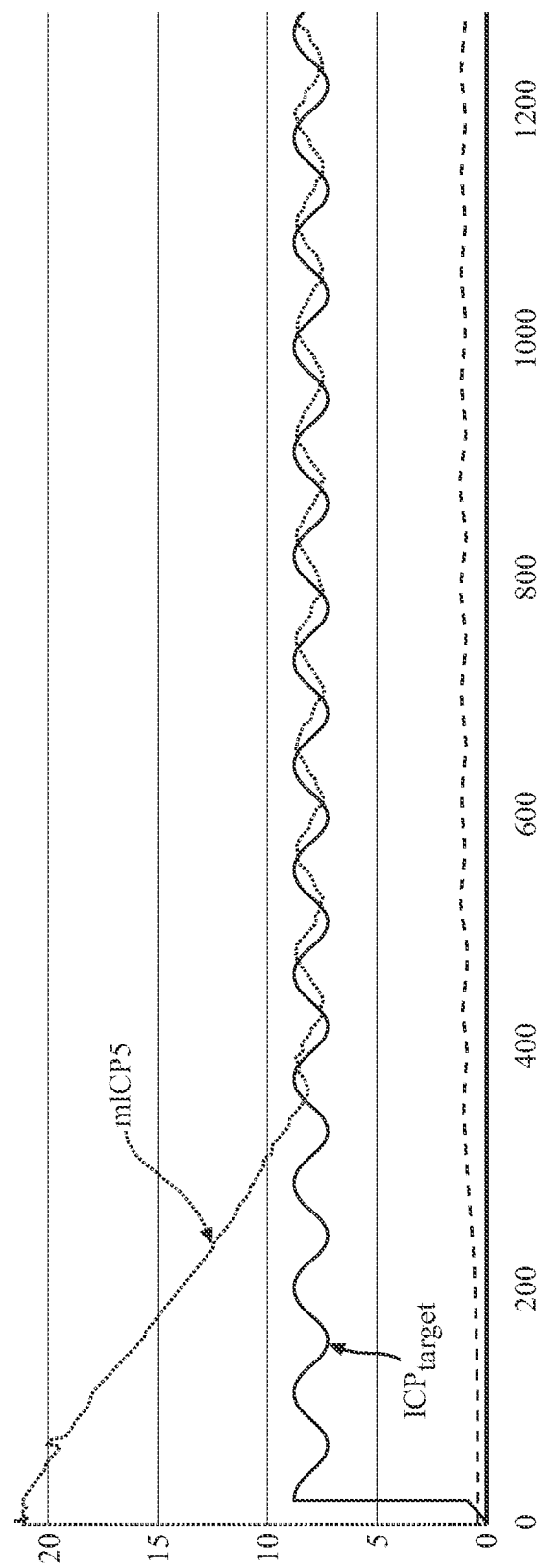
FIG. 7 shows pressure target $ICP_{target}$, mICP5 and true compliance.

FIG. 7 shows the pressure target parameter, $ICP_{target}$, mICP5 and the true compliance, for the same scenario as FIGS. 4-6. The initial ICP is 22 mmHg and is changed to around 8 mmHg by the controller. If mICP5 would become stable at exactly 8 mmHg, it would be impossible to estimate the compliance, because dP→0 and dV→0. In order to be able to continuously estimate the compliance, the $ICP_{target}$ signal is defined as a sinus-curve, i.e. an external modification of the target parameter. The amplitude and period of the sine is chosen such that reliable compliance estimation is achieved, while simultaneously ensuring appropriate target pressure values within a safe physiological range, i.e. without causing unnecessary risk to the patient. In this case the amplitude of the sinus curve is 0.75 mmHg and the period is 90 seconds, i.e. a frequency of approx. 0.011 Hz. As seen from FIG. 7 the $ICP_{target}$ is "ahead of" the mICP5 reflecting that the $ICP_{target}$ continually sets a new target for the pressure which introduces an offset that the control system continually tries to correct. The result is a slightly and controlled varying intra cranial pressure that makes it possible to estimate the compliance.

In FIGS. 4-7 the x-axes are seconds whereas the y-axes are mmHg.

The Flow Controller

Operation of the flow controller can be based on a control algorithm, such as a proportional-integral-derivative (PID) control, which is a well-established control loop feedback mechanism (controller) commonly used in industrial control systems. A PID structure is independent of the physical meaning of the process and control variables. A supervisory controller can be provided, which provides sufficient dependability to compensate for potential errors, for example in different sensors and/or actuators. Such a supervisory controller can subsequently be embedded in a real-time system.

The flow controller can be configured to continuously calculate an error value as the difference between a desired setpoint (target parameter) and a measured process parameter, such as the intracranial pressure signal, which can be provided by a pressure monitor implanted in the brain tissue. The controller can be configured to attempt to minimize the error over time by adjusting the rate of fluid in- and outflow to/from the subarachnoid space, i.e. this rate becomes a control variable.

The presently disclosed system can for example be configured to take ICP and $ICP_{target}$ as inputs, and output a desired volume flow $\Delta\dot{v}$. This output can then be translated into an infusion and an aspiration speed $\dot{v}_{in}$ and $\dot{v}_{out}$, taking into consideration the $FlowRate_{target}$, and limits on particular parameters such as $$\Delta\dot{v}, \frac{d}{dt}\Delta\dot{v}, \dot{v}_{in} \text{ and } \dot{v}_{out}.$$

These limits are continually updated based on a risk assessment (risk category), performed by the system.

Three risk groups can be defined based on the ICP and the estimated compliance $ĉ$, e.g.:
Low risk: −5<ICP<10 and 0.75<c<1.25
Medium risk: 10<ICP<20 or 0.50<c<0.75
High risk: 20<ICP<30 or 0.25<c<0.50

If the ICP or the compliance is out of all of the given ranges, the system is considered in a non-operational state, and the user is warned immediately.

A state machine can be implemented to further improve the stability and safety of the system. The state machine may be configured to have five states, which are entered in listed order:

Stopped indicating that the system has not been started or has been stopped.

Initializing during this state the system samples data from the pressure sensor and updates the DataProcessing class. The pump is not started.

PressureRamping during this state, the ICP is slowly ramped to the desired $ICP_{target}$ by aspirating/infusing fluid.

FlowRamping during this state, the flow rate is slowly ramped to the desired $FlowRate_{target}$.

Run in this state, both pressure and flow rate are maintained at the desired target values. Whenever the $ICP_{target}$ or $FlowRate_{target}$ are changed, e.g. through the user interface, the system re-enters the PressureRamping state.

The hardware for the presently disclosed systems and methods can be provided from existing technologies for ICP measurement and fluid in-/effusion control, such as pumps, tubing, sensors, catheters, liquids and liquid modifying systems. Pressure measurements can be provided by implantable pressure sensors (e.g Neurovent-P, Raumedic AG, Helmbrechts, Germany or SPC-350, USA) used for neuro-intensive care. Fluid infusion and aspiration can be performed with a programmable and high fidelity multi-channel pump (Reglo ICC, Ismatec, Wertheim, Germany) with a wide and suitable flow range (0.0002 to 35.0 mL/min) and standard I/O interface (RS-232 and USB 2.0). Fluid can be infused and aspirated through commercial tubing and catheters designed, approved and clinically used for cerebrospinal drainage in neuro-intensive care. Infused fluid may be standard Ringer Lactate, or other appropriate physiological solutions.

Preliminary Validation of Performance and Robustness Ex Vivo

Figure 8:
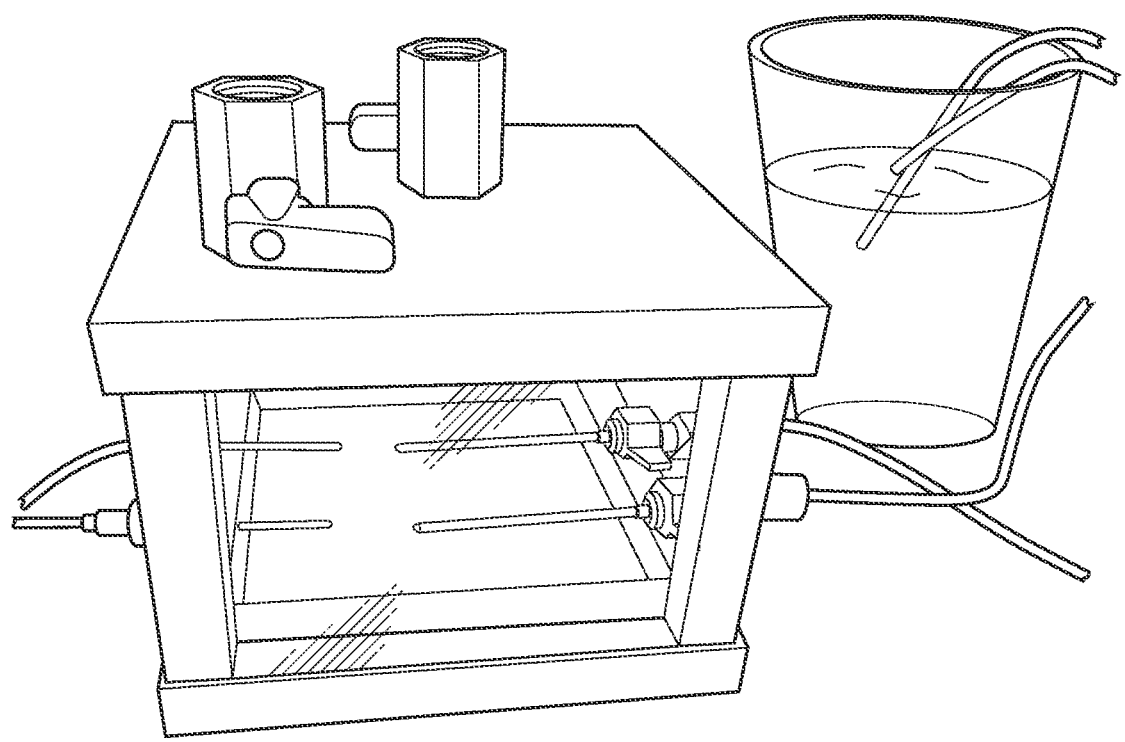
FIG. 8 shows and in vitro model of an intracranial compartment.
Figure 9:
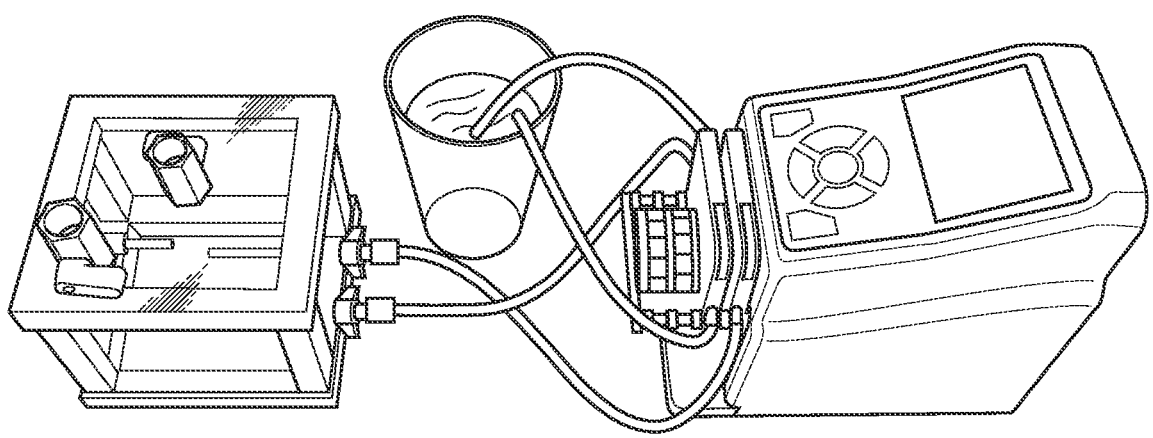
FIG. 9 shows an in vitro setup.

An ex vivo model of the intracranial space has been constructed to test and validate the presently disclosed concept as also illustrated in FIGS. 8 and 9. The model comprises a 100×100×70 mm airtight acrylic chamber with two separate valves, which allow for adjustment of the amount of saline/water and air in the chamber. The chamber is constructed from acrylic to mimic the rigid skull. The chamber is filled with both air and physiological isotonic saline in order to mimic the hydro-mechanical characteristics of the intracranial space. Saline will represent the non-compressible and interchangeable CSF, while air introduces hydro-mechanical capacitance, hence compliance, in the system. This allows for suitable changes in the volume of fluid in the chamber and provides a realistic pressure-volume relationship equivalent to that observed in the intracranial space of humans. The chamber is equipped with two separate bolt systems for flow catheter insertion and fixation (Medtronic, Inc. Silverline). These catheters provide pathways for fluid infusion and aspiration, i.e. controlled fluid exchange. The chamber also has two separate access points for insertion of pressure monitoring systems (Raumedic, Germany and Millar Instruments, Houston, TX, USA) for measuring the pressure inside the chamber. Both flow tubes will be connected to the fluid pump, which in turn will be controlled by the prototype controller using the pressure measurements as input variable. Flow catheters and pressure monitoring systems were positioned 1 cm over the bottom of the chamber. For the particular experiments presented, the chamber was filled with a 2 cm water column equivalent to a hydrostatic pressure of 1 cm $H_2O$. The valves were then closed to ensure first order damping effect of the remaining compressible air in the chamber. Compliance was in the range 0.1-0.4 mL/mmHg. The model allows for changes in the compliance and hydrostatic pressure by adjusting the air pressure and water column in the chamber.

Performance can be evaluated ex vivo over the entire flow range of the pump. Robustness and stability of the control algorithm can be evaluated using standard parameters, such as the minimum variance measure, the multiplicative perturbation, gain-phase margin, and the maximum singular value of the complementary sensitivity matrix. Closed-loop performance, including setpoint tracking and disturbance rejection/attenuation can be evaluated using the integral error measure and integral gain matrix singular value decomposition. These measures constitute standard estimates of robustness and performance for single- and multi-loop controllers. The controller has been adjusted to ensure sufficient stability and safety mechanisms have been employed to prevent excessive fluid aspiration or infusion and abrupt or unacceptable pressure changes (disturbance rejection). Thorough design space exploration have been conducted to tune the controller for apparent physiological scenarios. Robustness of the compliance estimation have been assessed for a wide range of predetermined compliance settings for the ex vivo model. Fluid volume and air volume/pressure have been adjusted to obtain a target value for estimation and system performance have been assessed using standard statistical estimates, such as the mean and variance of the estimate relative to the true value.

Example: Modelling and Testing the Physical System

Figure 3A:
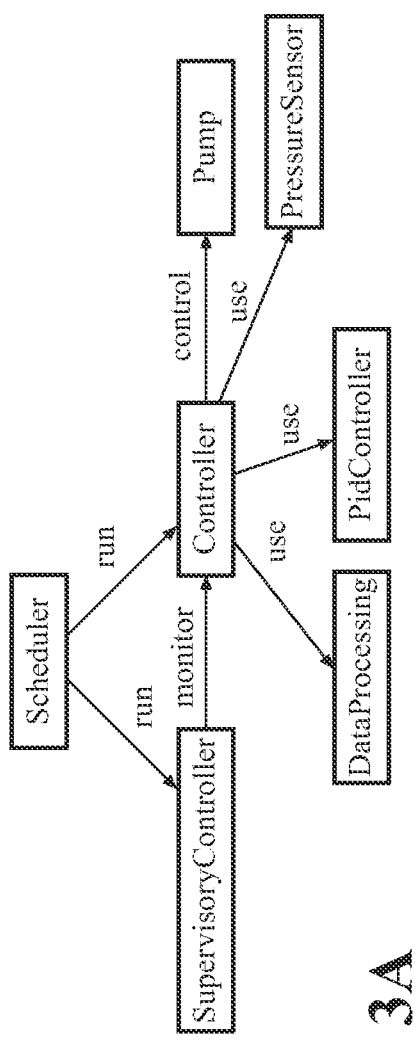
FIG. 3A shows a simplified class diagram of an exemplary control architecture for control of the presently disclosed system.
Figure 3B:
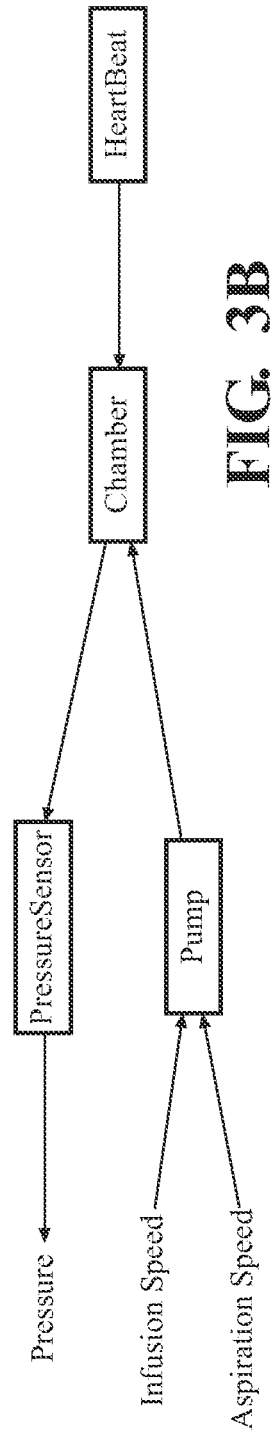
FIG. 3B shows a model of physical parts of a CSF system, modelled using 20-sim.

A model of the physical parts of the presently disclosed system has been constructed using the modeling and simulation program 20-sim (https://www.20sim.com/). The model consists of a pump, a chamber, and a heartbeat signal that affects the pressure in the chamber. FIG. 3B shows an overview of the model of the physical parts of the system used in 20-sim. The chamber is used as a model of the brain and intracranial space.

The discrete controller is implemented using the Vienna Development Method. This consists of a PID controller for controlling the flow in and out of the chamber, and a supervisory controller that monitors the process. The PID controller uses the measured pressure value to control the pump aspiration and infusion speed, in attempt to control the pressure inside the brain. The discrete controller has been code generated from VDM to Java using the Overture tool (http://overturetool.org/). The generated Java code is used to control the pressure in the chamber, when performing ex vivo experiments. Into-cps (http://into-cps.org/) uses a co-simulation engine to run both the discrete and continuous models and exchange the necessary parameters between them.

The ex vivo model consists of a Reglo ICC pump, fluid reservoir container, fluid waste container, ADC, Millar pressure sensor, chamber, and the software program that lets a user set parameters (e.g. target pressure, target flow rate) and controls the system. FIG. 1 shows an overview of how the ex vivo experiments can be set up, however with a fluid chamber instead of an actual body cavity. FIG. 9 shows the setup of the pump connected to the chamber and a fluid container.

In the exemplary embodiment in FIG. 1 the user (treating physician) defines a target pressure (e.g. 10 mmHg) and an average perfusion flow rate (e.g. 20 mL/min). These signals are fed to the control interface, together with the real-time intracranial pressure signal measured by a (pressure) sensor in the brain. The control interface sends output signals to a controllable high fidelity pump to maintain an average target perfusion rate and to produce small correctional flow changes that bring the measured pressure signal towards the target pressure signal (feedback error minimization).

Perfusion access is provided through a bi-directional double lumen catheter in the left lateral ventricle of the brain. The catheter flushes liquid from an external supply compartment, through the cerebrospinal fluid space and into an external waste reservoir. The control interface uses the measured pressure signal and the correctional flow signals to calculate the intracranial compliance in real-time. A supervisory controller ensures safe system operation and compensation for sensor and actuator errors. Alternative embodiments may be considered, e.g. using two catheters placed at different locations in the perfused compartment. The graphs show the results for an actual ex vivo experiment with the MVP. The MVP accurately estimates true initial compliance of 0.10 ml/mmHg, performs perfusion at the desired average rate of 20 mL/min, and steadily brings the ICP towards the target pressure of 10 mmHg as desired.

The experiments in this example (different from the setup in FIG. 1) is part of a prior step to testing the system in vivo. They will be used to validate the system accuracy and system response with different potential disturbances. The results of the experiments will indicate how accurate the system can control the pressure in the intracranial compartment.

Since the controller used in the ex vivo experiments, is directly generated from the VDM code that is used for simulation, the performance of the controller can be tested using the co-simulation tool. The performance of the controller with different inputs, different initial values etc., will give an idea of how well it will function in the ex vivo experiments. Therefore, if an error is found during the simulation, it can be fixed and tested again, before testing the controller on the ex vivo model.

Two types of tests will be performed in a simulation setting, ex vivo, and in vivo, namely step tests and disturbance tests:

Step tests are tests where different setpoint and initial values are tested, i.e. different steps between the initial and setpoint values are set (hence the name step tests). One setpoint is set; when the model system has controlled the process value to a steady state, a new setpoint is set. This type of test will show how well the system performs in different areas of pressure values. This will also help determine the linearity of the system. The purpose of the step tests is to test the accuracy and precision of the PID controller that controls the flow in and out of the brain, to reach a target pressure and target flow rate. This will be performed at different target and initial values of the pressure and flow rate, to examine the accuracy and precision at different levels.

Disturbance tests are tests where different disturbances are introduced to the model system to examine how the system reacts in such situations. Disturbance tests are usually based on real situations, such as a tube leakage or obstruction in the case of a CSF lavage device. These tests are usually performed in a critical environment to ensure the functionality of the controller in these states. The purpose of the disturbance tests is to verify that the system still functions as required under certain circumstances.

Figure 10:
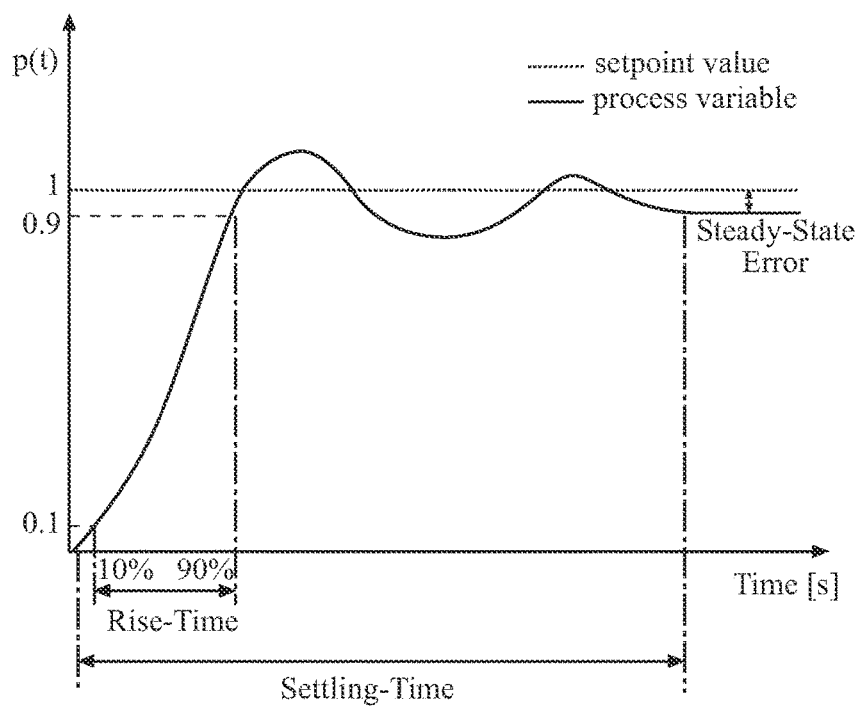
FIG. 10 illustrates the definition of the steady-state error, rise-time and the settling time relative to the setpoint value and the process value.

The stationary and transient response of the control system will be documented, specifically the steady-state error, rise-time and the settling time. The attributes and their descriptions can be found in Table 1 below and visualized in FIG. 10.

TABLE 1 system characteristics and their descriptions

| Attribute | Description |
|---|---|
| Steady-state error | Determine the error between the target pressure and process value (measured pressure). |
| Mean steady-state error | The mean of the steady-state error, when the target and process value are sine-curves. |
| Variance of steady-state error | The variance of the steady-state error, when the target and process value are sine-curves. |
| Rise-time | Determine how long it takes to get from 10% to 90% of the target pressure value. |
| Settling-time | Determine how long it takes in total to get from the initial pressure value to the value of the process value when the system is within a tolerance value of its steady-state. |

TABLE 2

The motivation for using these specific characteristics

| Attribute | Motivation |
|---|---|
| Steady-state error | Measure how accurate the PID controller can control the pressure in the brain (chamber). This value describes how well the PID Controller performs when it has reached its stationary state. |
| Mean steady-state error | The target and process value are sine-curves and therefore to find the accuracy of the PID controller, the mean of the steady-state error is calculated. |
| Variance of steady-state error | The precision of the PID controller is found by calculating the variance of the steady-state error. |
| Rise-time | This value is used to check that the controller corrects any difference between the measured pressure and the target pressure with an acceptable time range. Limits are defined for the supervisory controller to ensure that correction is not too fast or too slow. A too short rise-time may potentially cause damaging correctional fluid jets that may harm the patient or potentially cause instability of the controller. Too slow correction may result in undesirable intracranial pressures that could have been avoided if correction was faster. |
| Settling-time | This value is used to check the total time it takes the PID controller to control the pressure in the brain from the initial value to the stationary value. This value must not be too high: the controller's output may be fluctuating until it reaches a steady state, which is undesired if it takes too long, the system may not fulfill the needs of controlling the patient's pressure if it takes longer than manually controlling the pressure, the system performance is low |

The motivation to document these specific parameters is described in Table 2 above and they can be logged in different ways.

A sine curve is added to the target pressure to allow calculating the compliance value:

$$\text{compliance} = \frac{dV}{dP}$$

If the target pressure was a constant, then the measured pressure would reach a constant value, which would give a difference of 0 when differentiating. This would lead to dividing the volume with 0, which is not possible.

Figure 11:
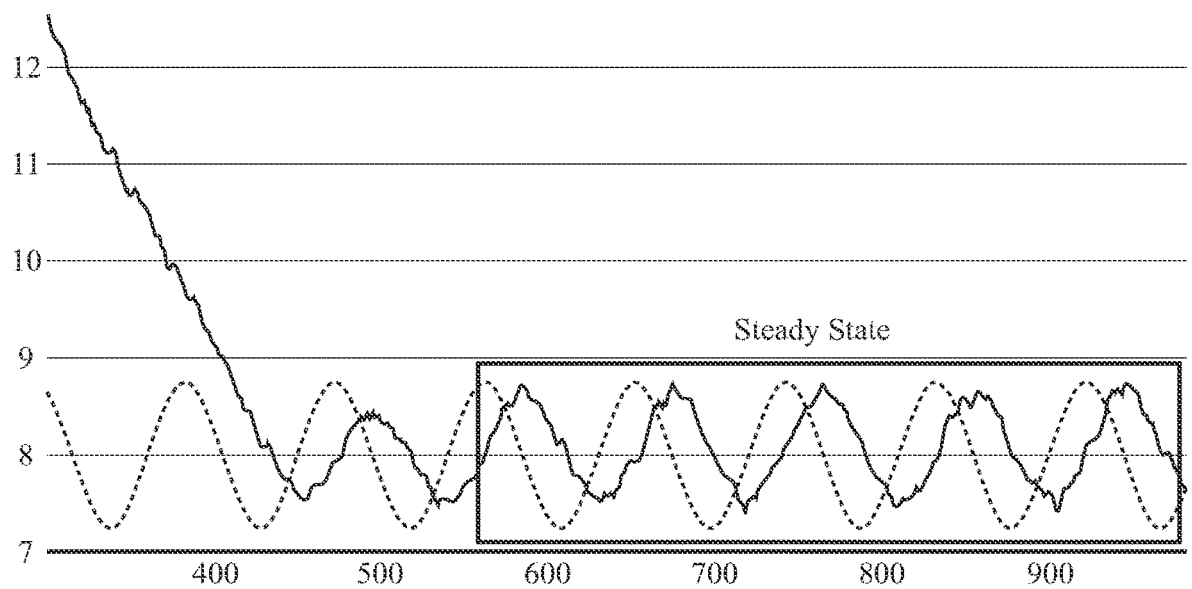
FIG. 11 illustrates an example of an area where the system is in steady state.

To find the steady-state and thus the steady-state error and settling time, the mean value and variance of the measured pressure will be analyzed. The steady state will be defined as the moment where the mean and variance of the measured pressure signal is constant within a tolerance of +/−0.2 mmHg for two periods of the sine curve. The mean value will be calculated using a moving average over two periods of the sine-curve. FIG. 11 shows an example of an area where the system is in steady state.

Mean Steady-State Error (Accuracy)

The mean error signal (difference between the target and measured pressure) will be calculated when the system is in its steady state. This will be defined as the accuracy of the system.

Variance of the Steady-State Error (Precision)

The variance of the error signal (difference between the target and measured pressure) will be calculated when the system is in its steady state. This will be defined as the precision of the system.

Settling-Time

The settling-time will be measured as the time it takes from the start of the experiment until the system is in steady state.

Rise-Time

The rise-time will be measured as the time it takes the system to go from 10% up to 90% of the target value.

This section will describe the parameters that will be set when performing different simulation tests, and the motivation for choosing these parameters, and their values. Apart from that the method for performing the tests using the into-cps application will be described. Table 3 below describes the parameters that are varied in the simulation tests.

TABLE 3

Description of the parameters that can be set in the simulations and which tests they are used in

| Parameters | Description | Use in test type |
|---|---|---|
| Initial pressure [mmHg] | The initial value of the pressure in the chamber | Step + Disturbance |
| Target pressure [mmHg] | The target value of the pressure | Step + Disturbance |
| Compliance [ml/mmHg] | $\frac{dV}{dP}$ | Step + Disturbance |
| Target flow rate [ml/min] | The target value of the flow rate | Step + Disturbance |
| Measured pressure noise | Noise added to the measured pressure value. The noise will be added to the pressure value in the output of the continuous model to the discrete model. The noise is multiplied with a square signal to allow inputting noise to the system in intervals. The discrete PID controller will therefore receive a pressure value with noise added to it. | Disturbance |
| $K_{infusion}$ | Constant value K multiplied with output of the pump infusion value, so the infusion into the brain (chamber) will be scaled by $K_{infusion}$. | Disturbance |
| $K_{aspiration}$ | Constant value K multiplied with output of the pump pump aspiration value, so the aspiration out of the brain (chamber) will be scaled by $K_{aspiration}$. | Disturbance |

The last three parameters are added to the model created in 20-sim, where it is possible to change these values in into-cps when performing co-simulations.

The motivation for choosing the first four parameters in Table 3 is to test the system in different operational states. The initial pressure and compliance will be different depending on the patient and their condition. The values that will be chosen as target pressure and flow rate will also vary depending on the patient and their condition. Therefore, it makes sense to test with different potential values, to simulate different patients with different brain conditions.

The motivation for adding noise to the measured pressure value is an attempt to simulate a nurse moving the equipment around, and therefore possibly introducing noise in the device including noise due to manipulation of the pressure sensor.

The motivation for multiplying the aspiration and infusion values with a constant, is an attempt to simulate a leakage or obstruction in the tubes between the pump and the brain (chamber). It is important to note that assumptions have been made when simulating a leakage. In reality, leakage is a function of the pressure difference in the chamber and the tubes. In this case it is assumed that there is no pressure difference between the chamber and the tubes.

TABLE 4

Description of the values that will be measured when performing the simulations

| Value | Description |
|---|---|
| Simulation time [s] | The simulated time passed. |
| Compliance [ml/mmHg] | The compliance is: $\frac{dV}{dP}$, and it is used to calculate the risk group of the patient. It is used to check that the risk group is calculated correctly. |
| Varying pressure setpoint [mmHg] | A sine function is added to the constant pressure setpoint, to allow measuring the compliance. If it was not added, the pressure will be constant at a point, thus the compliance could not be calculated due to a division with 0. This is the target pressure value and will be used to calculate the steady-state error of the PID controller. |
| Infusion pump speed [ml/min] | The value of the pump infusion speed that the PID controller sets. This value will be used to check that the supervisory controller limits the PID controller's output according to the current risk group. |
| Aspiration pump speed [ml/min] | The value of the pump aspiration speed that the PID controller sets. This value will be used to check that the supervisory controller limits the PID controller's output according to the current risk group. |
| Calculated risk | The risk that is calculated at each step in the simulation. This is calculated by the supervisory controller. This will be used to check that the supervisory controller calculates the risk correctly. |
| Measured pressure [mmHg] | The measured pressure from the continuous model. This value will be used to calculate the steady-state error of the PID controller. It will be compared with the varying pressure setpoint. |

The into-cps application is used to perform the co-simulation step and disturbance tests of the system.

The design space exploration functionality (dse) in into-cps, will be used to perform an exhaustive test of the system with a defined set of parameter values. The defined set of parameter values is different depending on the type of test, i.e. step tests and disturbance tests. The parameter values will be set to a constant value during the complete simulation. Each time a new combination is tested, a new simulation is run.

The parameters will be set in the into-cps application before running dse. When running a dse, all the possible combinations of parameter values will be run. The pressure-Setpoint (target pressure) parameter is set to be 8 and 15, and the initial chamber air pressure is set to be the values 10 and 15. When a dse is run with these settings, it will perform combinations, where it will run 4 simulations, with the settings:

1. {Pressure setpoint: 8, Initial chamber air pressure: 10}
2. {Pressure setpoint: 8, Initial chamber air pressure: 20}
3. {Pressure setpoint: 15, Initial chamber air pressure: 10}
4. {Pressure setpoint: 15, Initial chamber air pressure: 20}

The output thereof can be plotted and used for visual inspection. Example of such plots are shown in FIG. 12-14.

Step Tests

The parameter values that are chosen to be tested in the step tests are written in table 5 below.

TABLE 5

The parameter values that will be tested with in the step test simulations

| Parameter | Values |
| --- | --- |
| Initial pressure [mmHg] | {0, 5, 10, 15, 20} |
| Target pressure [mmHg] | {0, 5, 10, 15, 20} |
| Target flow rate [ml/min] | {0, 1, 2} |
| Initial compliance [ml/mmHg] | {0.26, 0.65, 1.24} |

The initial and target pressure values are chosen with a distance in between, to test different combinations within different risk groups. The boundary values (0 and 20 in this example) are being tested. The most typical target flow rates that will be set on the device are the values described in Table 5. The value 0 ml/min represents the situation where no net perfusion is conducted. The boundary values of the compliance are set as initial values to test them.

Disturbance Tests

The parameter values that are chosen to be tested in the disturbance tests are written in table 6 below.

TABLE 6

The parameter values that will be tested with in the disturbance simulations

| Parameter | Values |
| --- | --- |
| Initial pressure [mmHg] | {10, 20} |
| Target pressure [mmHg] | {10, 20} |
| Target flow rate [ml/min] | {0, 1, 2} |
| Initial compliance [ml/mmHg] | {0.26, 0.65, 1.24} |
| Measured pressure noise (amplitude, variance and duration [s]) | Amplitude: {1, 3} Variance: {0.5, 1} Duration: {1, 8, 15} |
| $K_{infusion}$ | {0.5, 1.5} |
| $K_{aspiration}$ | {0.5, 1.5} |

The motivation for choosing the initial and target pressure to be 10, is that it is a safe and average pressure value for the brain. The motivation for choosing the initial and target pressure to be 20, is that it is a critical value, it is desired to perform disturbance tests of the system in a critical state. The motivation for choosing the K values to be 0.5 and 1.5, i.e. below and above 1, is to simulate a leakage or an obstruction in the tube, where part of the fluid is lost or retained in the chamber. The noise will be added to the pressure in intervals as shown in FIG. 15, to simulate a noisy pressure sensor.

When performing the experiments ex vivo, it is important to note the accuracy of the pump and sensor used, since this will affect the results. Ex vivo experiments will generally follow the exact same pattern as described above for the simulations. Controller precision and accuracy will be determined using step tests.

Compliance will be estimated continuously during the step-tests. Before and after each step-test, we will determine the pressure volume curve of the chamber at predefined initial water levels and air pressures (i.e. baseline compliance and pressure), by infusing a predefined small volume of incompressible liquid in the chamber and varying water levels and recording the resulting pressure change. The pressure volume curve will serve as a reference for comparison of the calculated compliance reported by the device during the step test.

Example: In Vitro Tests and Compliance Tests

Figure 12A:
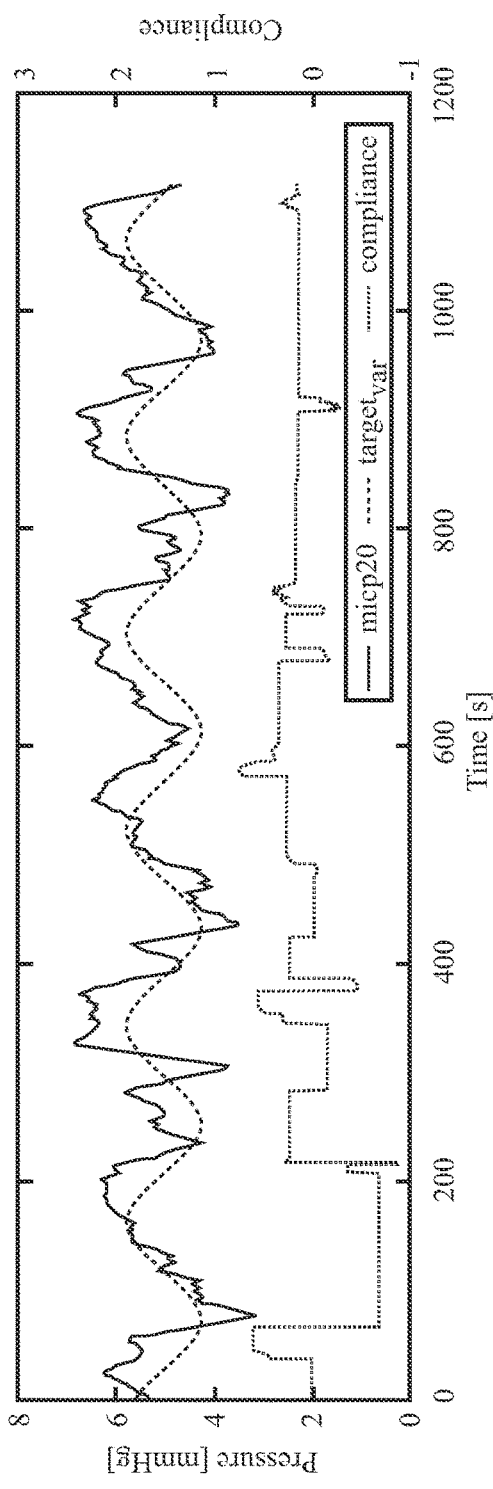
FIGS. 12-14 show different in vitro step tests performed using a chamber.
Figure 12B:
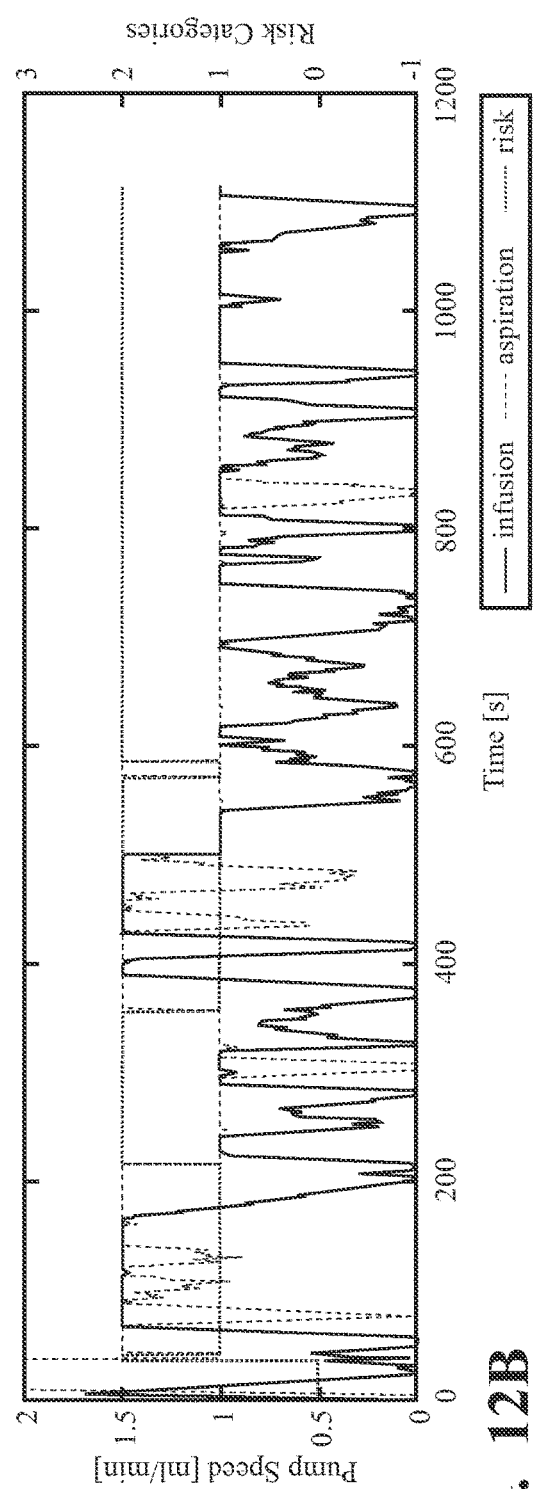
Figure 13A:
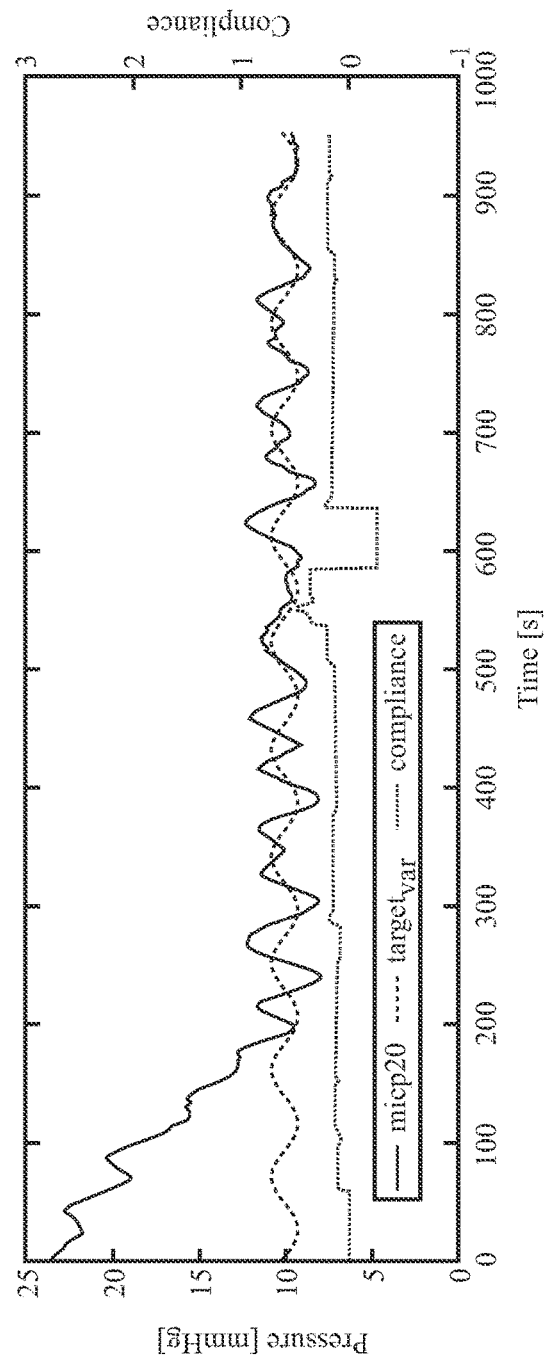
Figure 13B:
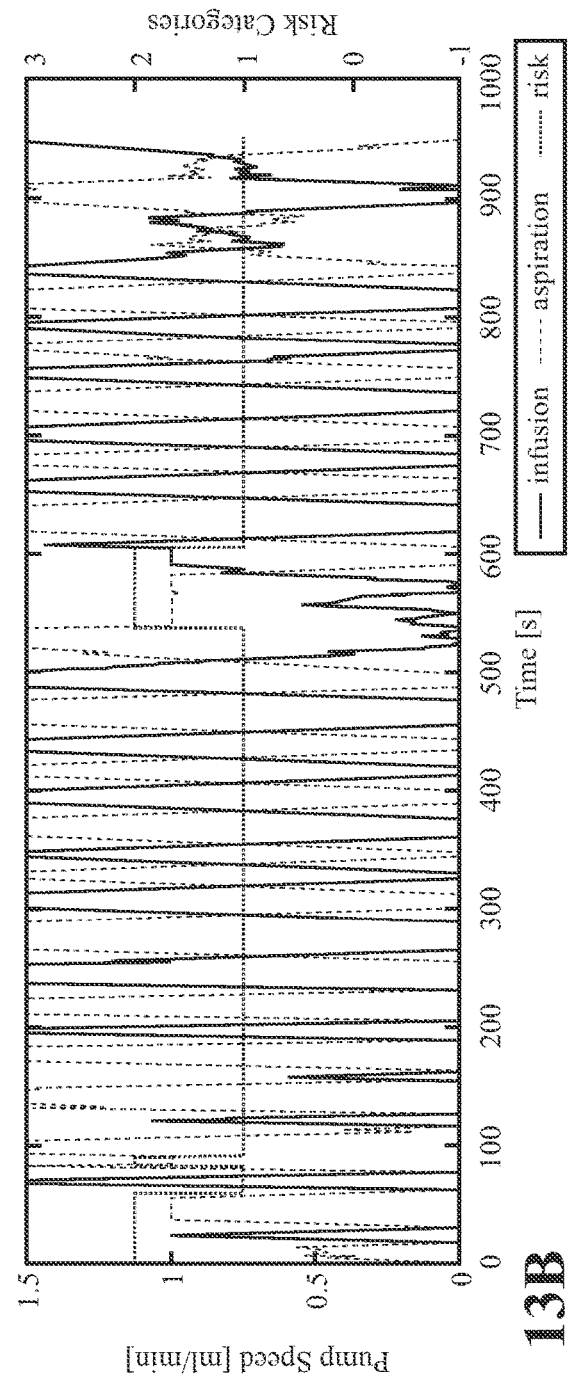
Figure 14A:
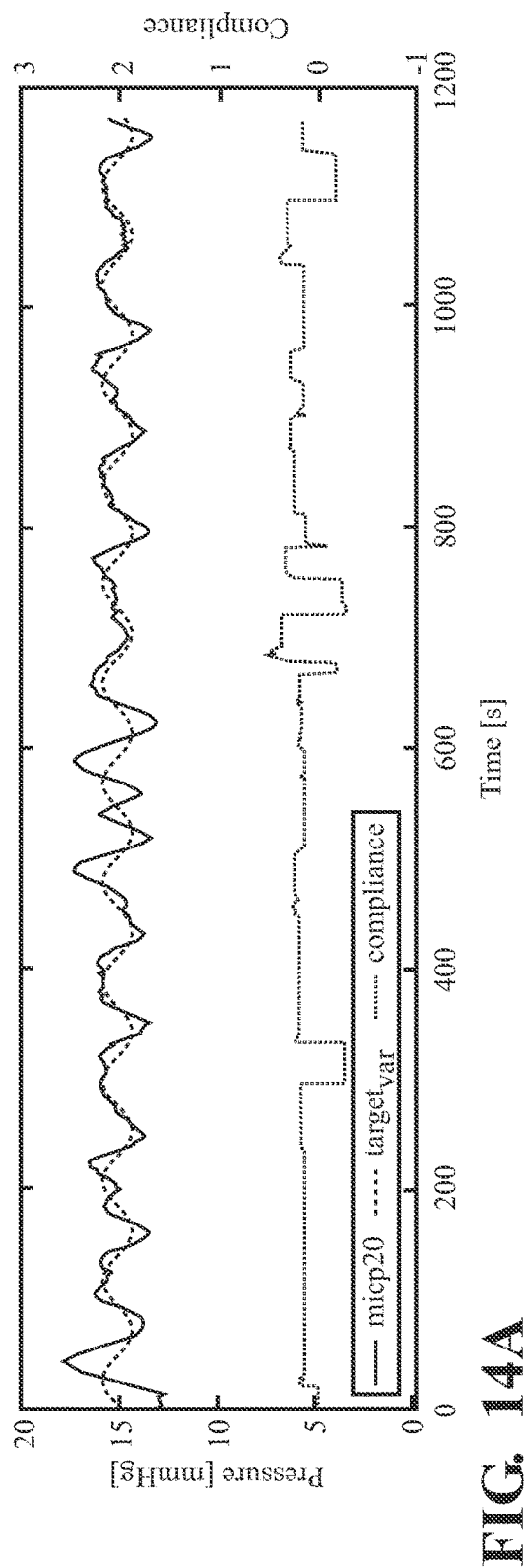
Figure 14B:
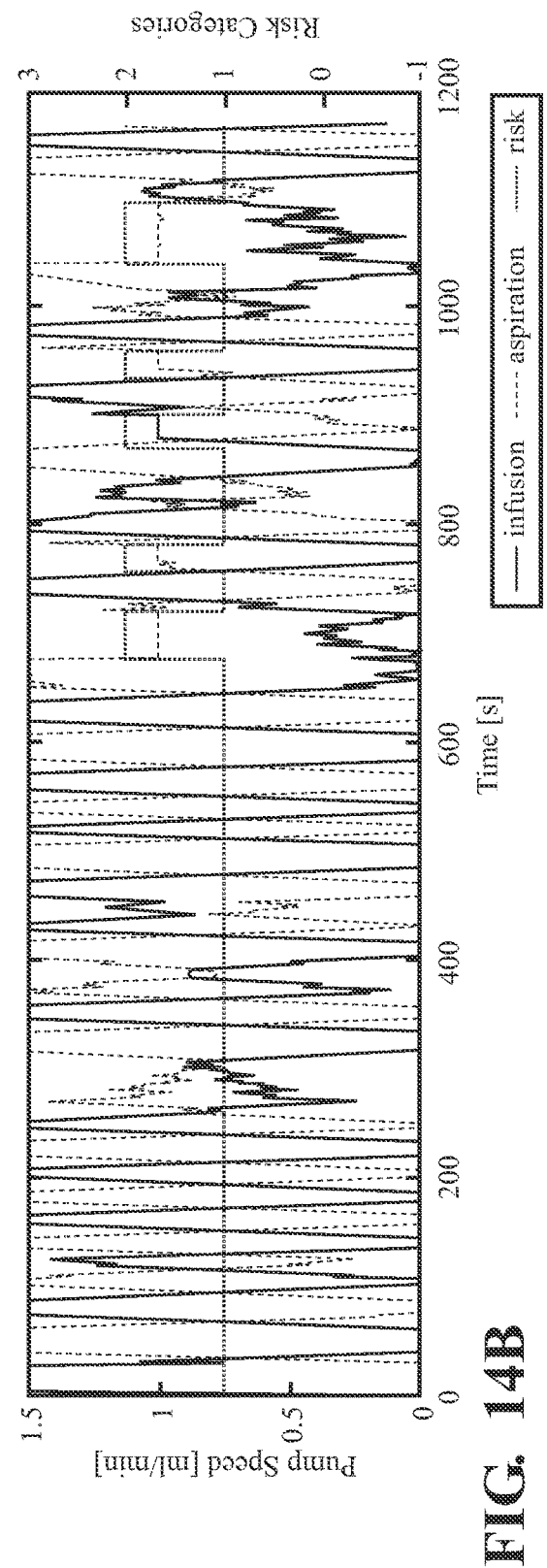

Different in vitro tests were performed with focus on validating the compliance calculated with the real compliance of the chamber. Step tests were performed to validate the system functionality and illustrated in FIG. 12 where the pressure setpoint was 5 mmHg, in FIG. 13 where the pressure setpoint was 10 mmHg, and in FIG. 14 where the pressure setpoint was 15 mmHg. In FIGS. 12A, 13A and 14A time is on the X-axis in seconds, pressure in mmHg is on the left Y-axis for the two upper curves where one is micp20 (pressure filtered with moving average over 20 seconds, in black) and the other is the stable varying target pressure (in red). The right Y-axis denotes the calculated compliance (thick blue line). FIGS. 12B, 13B and 14B correlates with FIGS. 12A, 13A and 14A on the X-axis time scale and show the infusion pump speed (in green) and the aspiration pump speed (in purple) denoted by the left Y-axis with pump speed measured in [ml/min] and the associated risk category (in cyan) on the right Y-axis.

The compliance tests were performed by running a normal step test on the system. When the pressure had reached a stable value, the system was turned off, and all the data was saved.

The real compliance of the system was then measured by performing the following:

1. Seal the ends of the pump tubes, to maintain the same pressure
2. Register the pressure value
3. Use a syringe to inject 3 ml of water into the chamber
4. Register the pressure value
5. Use the syringe to remove 3 ml of water from the chamber
6. Register the pressure value
7. Use the syringe to inject 3 ml of water into the chamber Perform steps 2-7 a few times. Then use the data to calculate the real compliance of the chamber.

The real compliance was compared with the calculated compliance. Where the median and mode of the whole compliance during steady state was calculated. An example of some of the values are shown in the table below

| Target Pressure | Real compliance (+/−3 ml) | Real compliance (+/−5 ml) | Median compliance | Mode compliance |
| --- | --- | --- | --- | --- |
| 5 | 0.35 | 0.33 | 0.11 | 0.10 |
| 10 | 0.32 | 0.33 | 0.16 | 0.12 |
| 15 | 0.32 | 0.33 | 0.17 | 0.18 |

It was expected that the compliance would change under different pressure setpoints, but as shown in the data above, it was nearly the same under different pressure setpoints. The reason for this is probably that the pressure range where the compliance of the chamber was measured, was not large enough.

Figure 16:
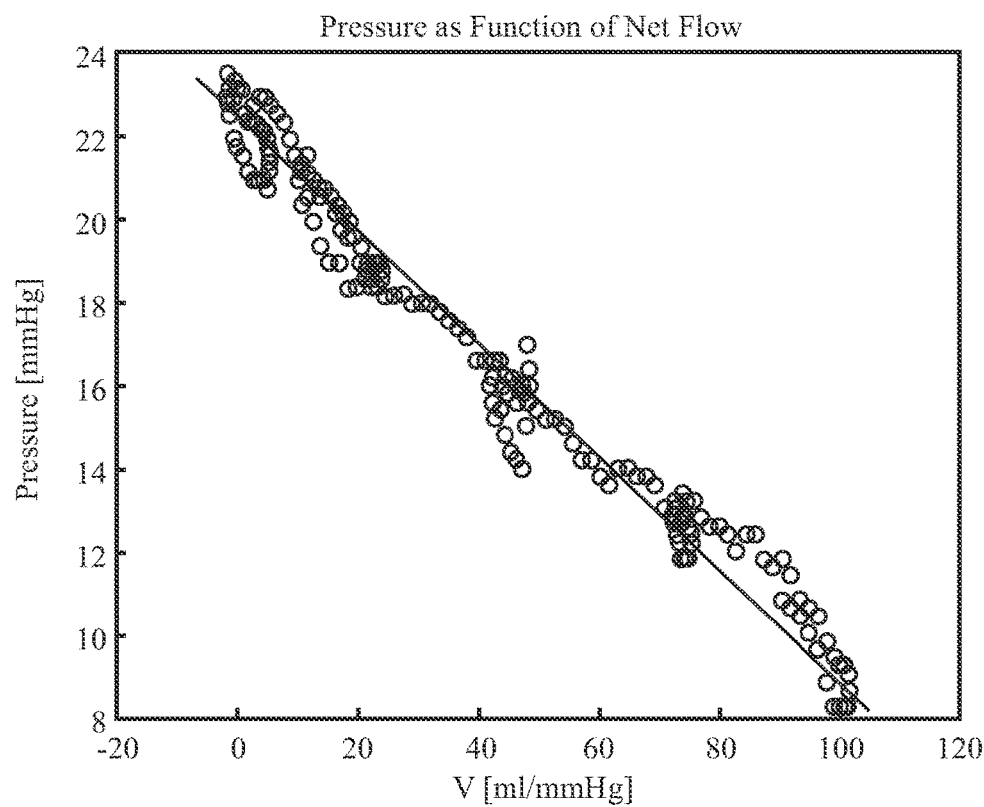
FIG. 16 shows pressure plotted as a function of the net flow; obtained during an in vitro test. The initial pressure was around 20 mmHg, and the setpoint was 10 mmHg. The plot is from the area where the pressure was settling down to 10 mmHg. The y-axis is the measured pressure. The x-axis is the cumulative sum of the volume flow ($dv=v_{out}-v_{in}$) and linear regression has been provided.

The pressure can be plotted as a function of the net flow, as shown in FIG. 16. The results are from an in vitro test, where the initial pressure was around 20 mmHg, and the setpoint was 10 mmHg. The plot is from the area where the pressure was settling down to 10 mmHg. The y-axis is the measured pressure. The x-axis is the cumulative sum of the volume flow ($dv=v_{out}-v_{in}$) and linear regression has been provided as illustrated in FIG. 16.

The calculation of the compliance was also performed in the simulation of the system. Where the real compliance of the plant was used as the "real" value, and the calculated compliance was compared to the real value. Two simulations were performed, where the focus was on the compliance and the results are shown in FIGS. 33-34 where time is in the X-axis in seconds, and compliance as the y-axis in ml/mmHg.

Test #1 (FIG. 33): Initial pressure: 5 mmHg, Target pressure: 5 mmHg, Flow rate: 0 ml/hr, initial compliance: 0.26 ml/mmHg Test #2 (FIG. 34): Initial pressure: 5 mmHg, Target pressure: 5 mmHg, Flow rate: 60 ml/hr, initial compliance: 0.26 ml/mmHg In the plots in FIGS. 33-34 the plant compliance is illustrated in green and is estimated using three different filtering methods: "Integrate the flow and threshold" in blue dots, median filtered in red dots and exponential low-pass filtered in the cyan line.

Figure 33:
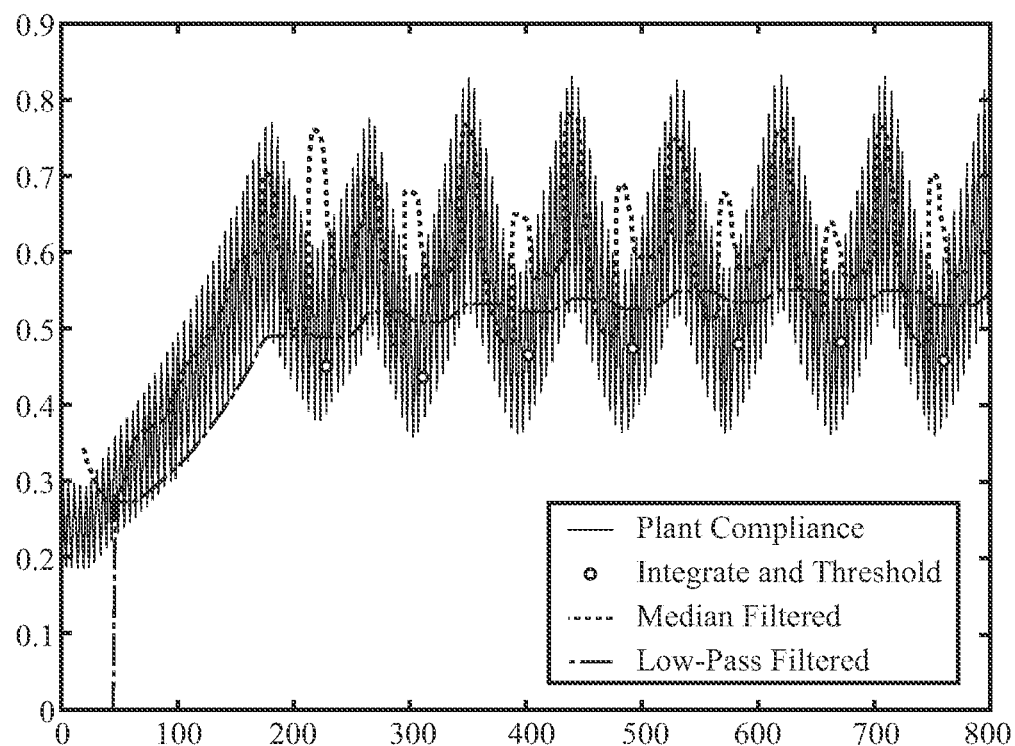
FIGS. 33-34 shows comparison between calculated and simulated compliance in a chamber using three different filtering methods.
Figure 34:
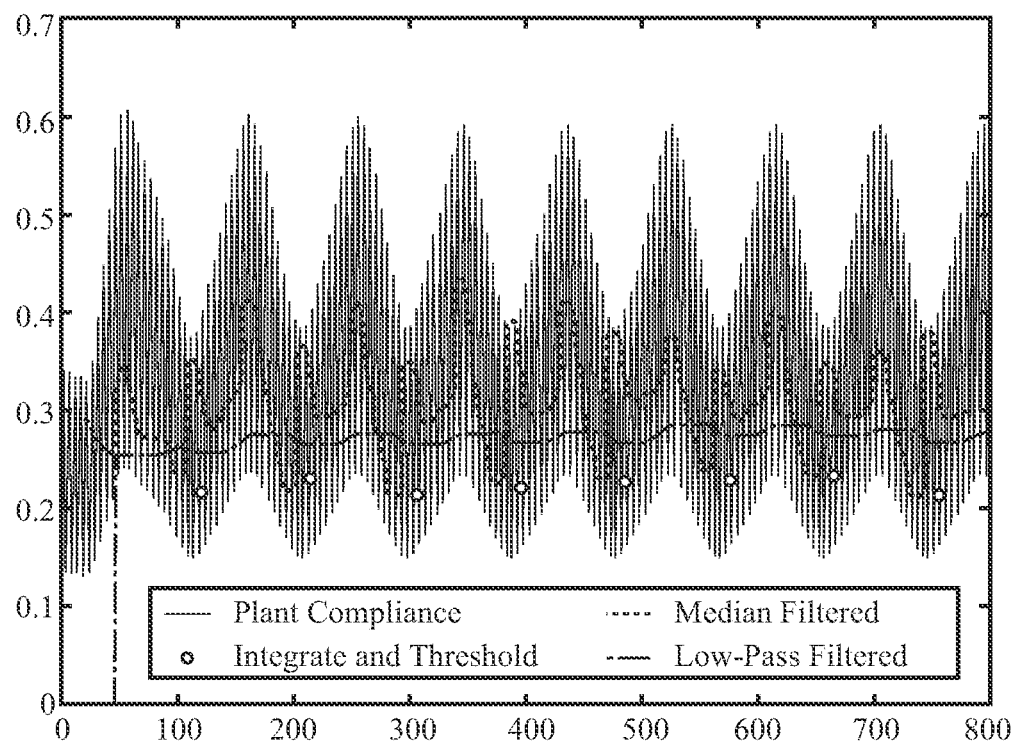

As seen in FIGS. 33-34 the median filtering and low-pass filtering continuously calculates the compliance, while the "Integrate the flow and threshold" filtering method only calculates the compliance when specific thresholds are exceeded. As also seen the median filtering does not fit the data very well, whereas the "Integrate the flow and threshold" filtering method fits the data but is a bit lower. The low-pass filtering method often fits the data and the calculated compliance is quite stable.

Example: Simulation of Compliance

The exemplary CSF Lavage Device was simulated with 1) Step tests in order to simulate the system with different pressure target values, and 2) Disturbance Tests in order to simulate potential disturbances in the system, e.g. tube leakage.

Figure 18:
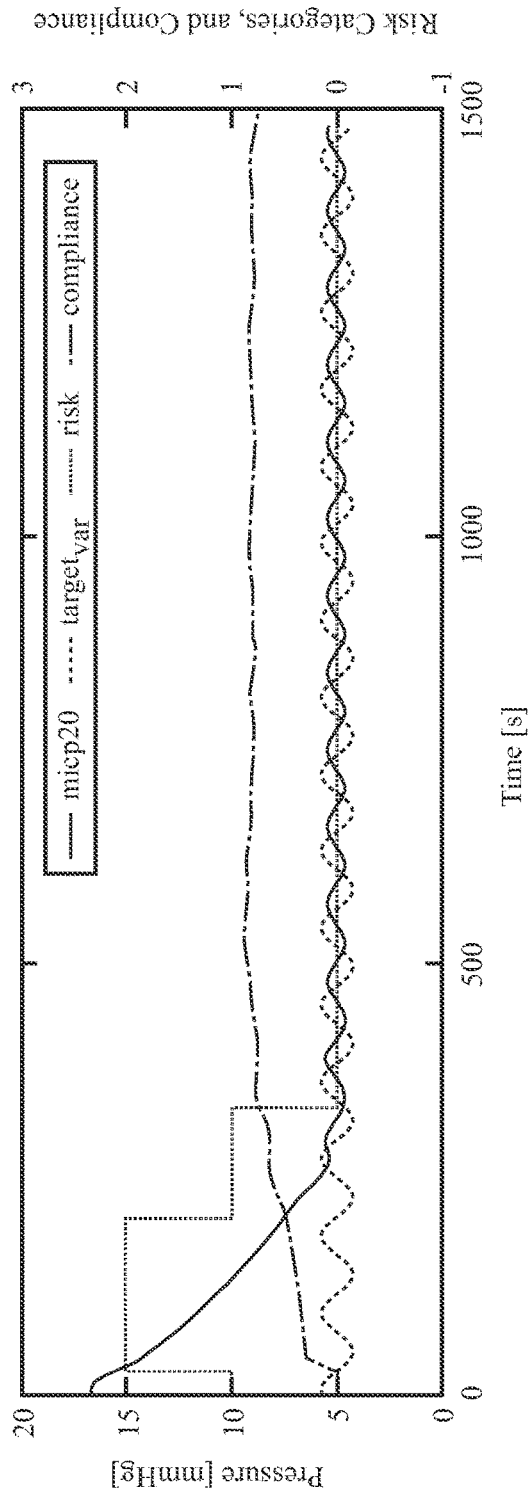
FIG. 18 shows an example of a step test simulation.
Figure 19:
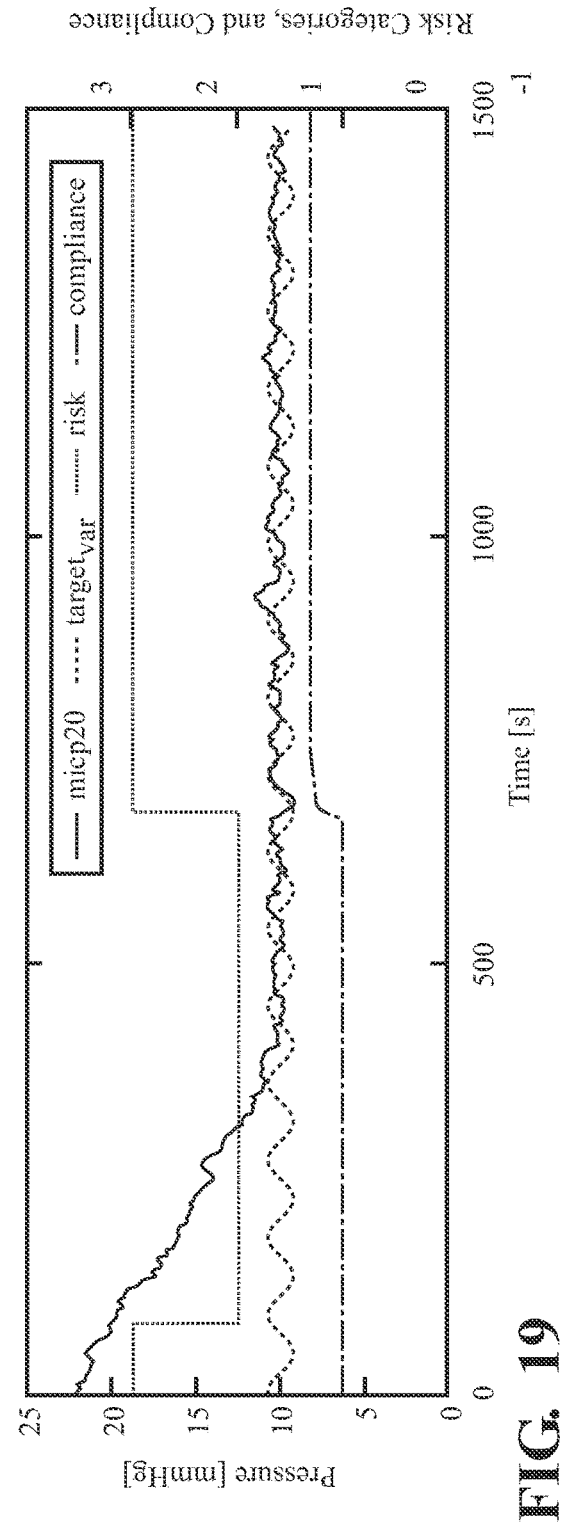
FIG. 19 shows an example of a disturbance test simulation.
Figure 20:
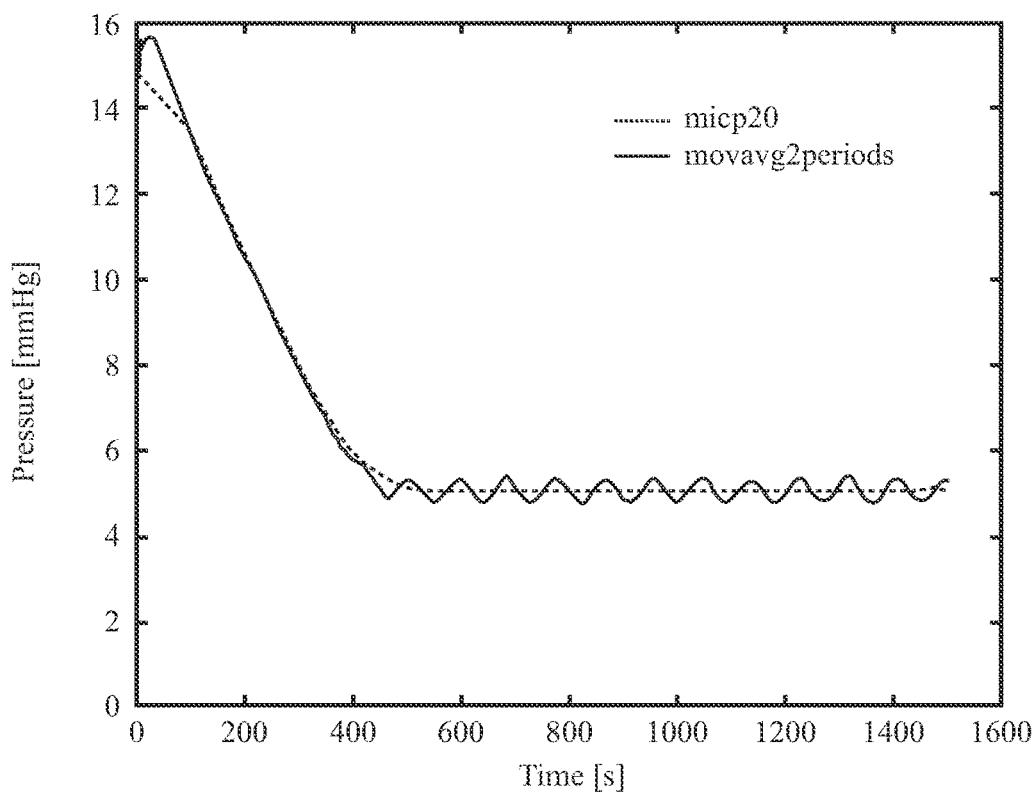
FIGS. 20-21 illustrate an example of how to find the steady state area by filtering the signal with a moving average over two sine periods (FIG. 20), then differentiating the signal, and finding the point where the signal is 0 (FIG. 21).
Figure 21:
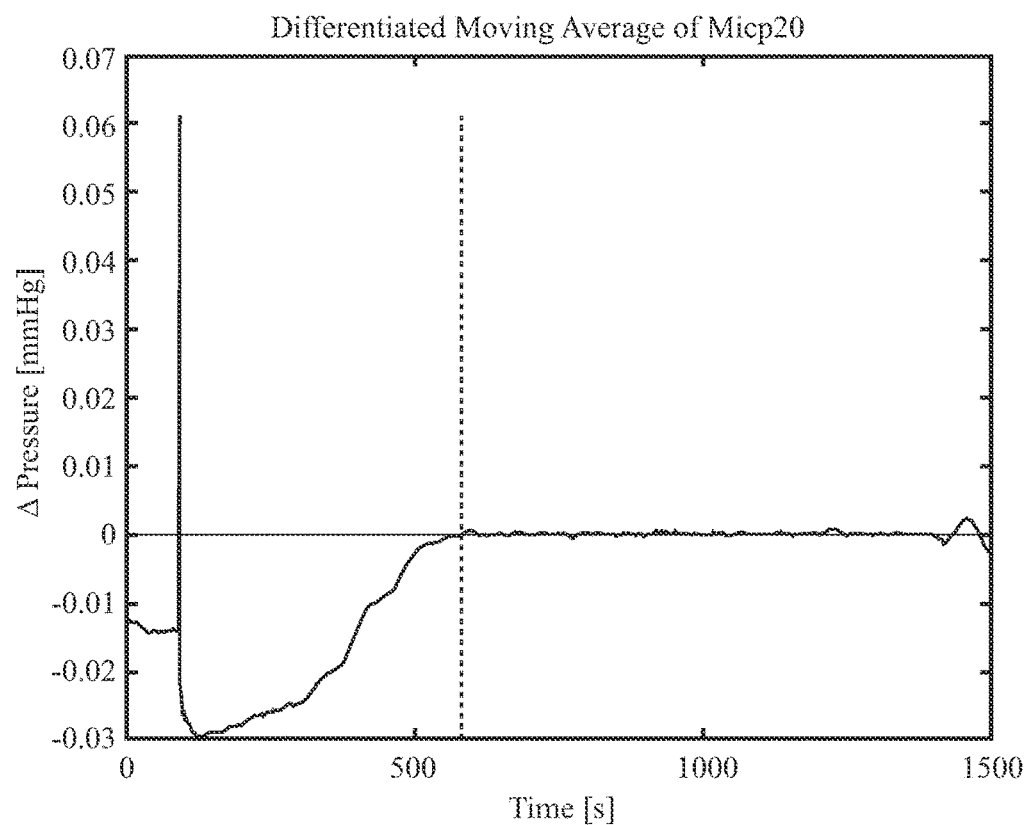

FIG. 18 shows a step test simulation example with the following settings:
Initial pressure: 15 mmHg
Target pressure (target_var): 5 mmHg
Micp20: Pressure filtered with moving average over 20 seconds FIG. 19 shows a disturbance test simulation example with the following settings:
Initial pressure: 20 mmHg
Target pressure (target_var): 10 mmHg
Micp20: Pressure filtered with moving average over 20 seconds
Pump infusion and aspiration tube leakage of 50%
Noise in pressure measurement with amplitude of 3 mmHg, on/off every 15 seconds The result analysis follows the approach listed above in tables 1 and 2. As illustrated in FIGS. 20 and 21 The steady state area is found by filtering the signal with a moving average over two sine periods, then differentiating the signal, and finding the point where the signal is 0.

The parameters experimented with in the step tests are as follows:
The initial pressure values (0, 5, 10, 15, 20), are chosen to test the system in realistic and extreme conditions. These indicate the pressure value when starting the simulation.

The target pressure values are chosen to test the system in the typical scenarios (5, 10, 15), and the more extreme scenarios (0, 20).

The target flow rate values (0, 1, 2) are chosen to test the system in the typical scenarios.

The initial compliance values are chosen to test the boundaries (0.26, 1.24) and a value in between (0.65).

Three risk groups can be defined based on the ICP and the estimated compliance $\hat{c}$, e.g.:
Low risk: $-5<ICP<10$ and $0.75<c<1.25$
Medium risk: $10<ICP<20$ or $0.50<c<0.75$
High risk: $20<ICP<30$ or $0.25<c<0.50$ The parameters experimented with in the disturbance tests are:
The initial pressure values (10, 20).
The target pressure values (10, 20). The motivation for choosing the initial and target pressure to be 10, is that it is a safe and average pressure value for the brain. The motivation for choosing the initial and target pressure to be 20, is that it is a critical value, it is desired to perform disturbance tests of the system in a critical state.
The target flow rate values (0, 1, 2) are chosen to test the system in the typical scenarios.
The initial compliance values are chosen to test the boundaries (0.26, 1.24) and a value in between (0.65).
Measured pressure noise (amplitude (1, 3) and duration (8, 15))
$K_{infusion}$ (0.5, 1.5) and $K_{aspiration}$ (0.5, 1.5). The motivation for choosing the K values to be 0.5 and 1.5, i.e. below and above 1, is to simulate a leakage or an obstruction in the tube, where part of the fluid is lost or retained in the chamber.

Figure 17:
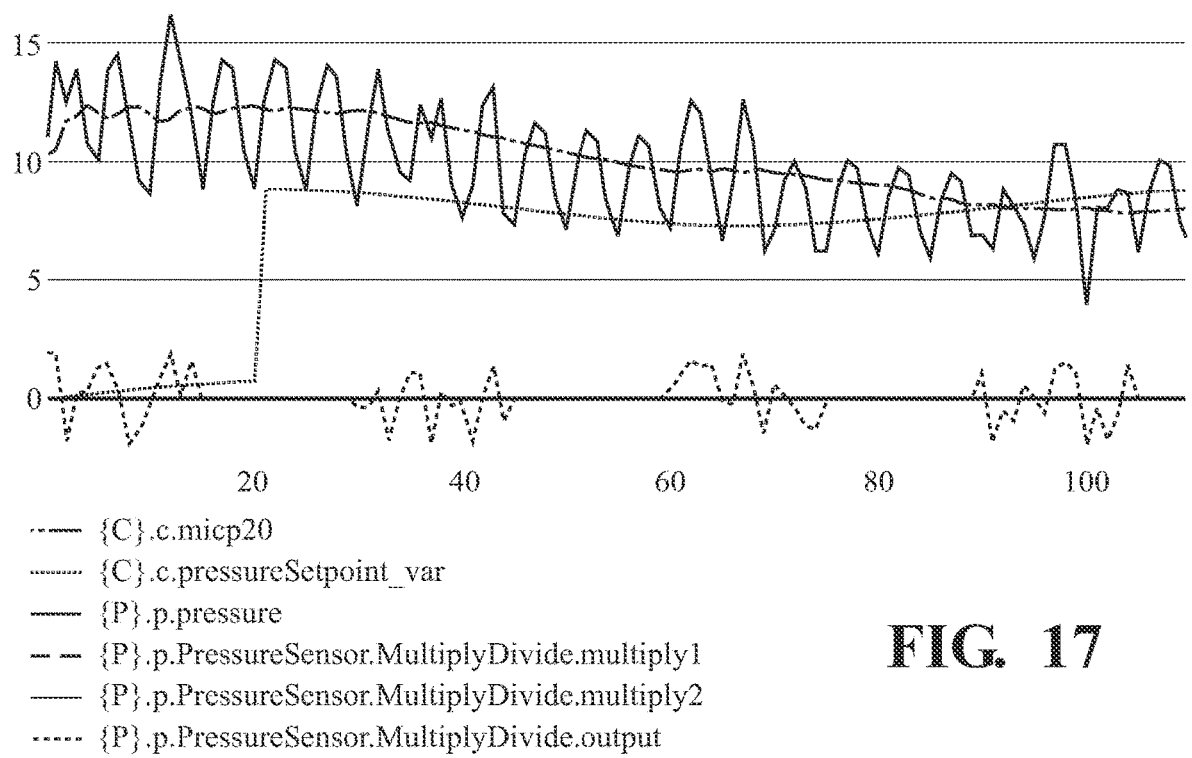
FIG. 17 shows the result of noise added to the pressure signal in periods of a defined length, in this case 8 and 15 seconds, respectively.

As shown in FIG. 17 the noise is added to the pressure signal in periods of a defined length. The lengths experimented with are 8 s and 15 s. The brown signal (lower curve in FIG. 17) is the noise that is added to the pressure signal. The green signal (upper varying curve) is the pressure signal with the noise added to it.

Figure 22:
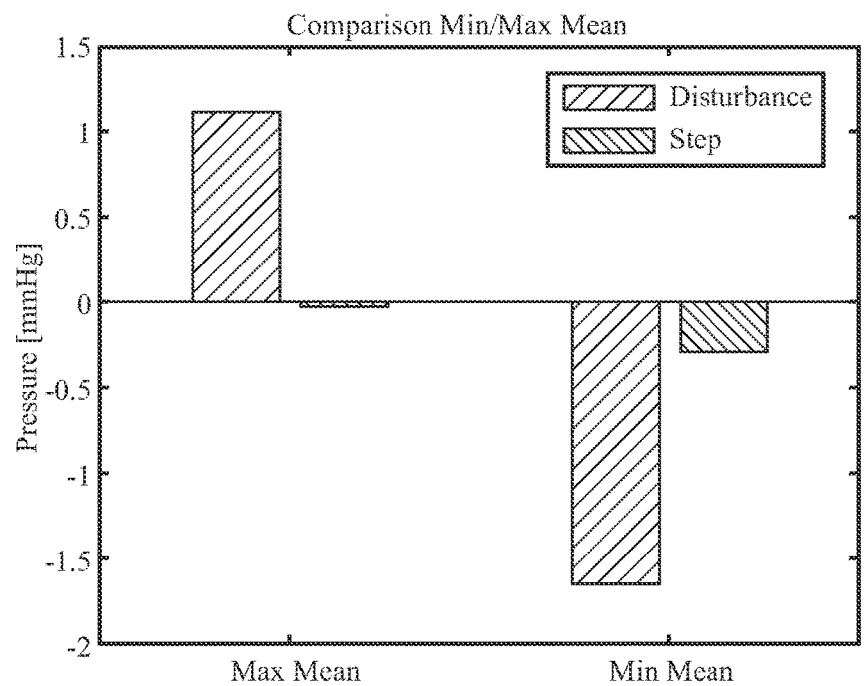
Figures 23, 24:
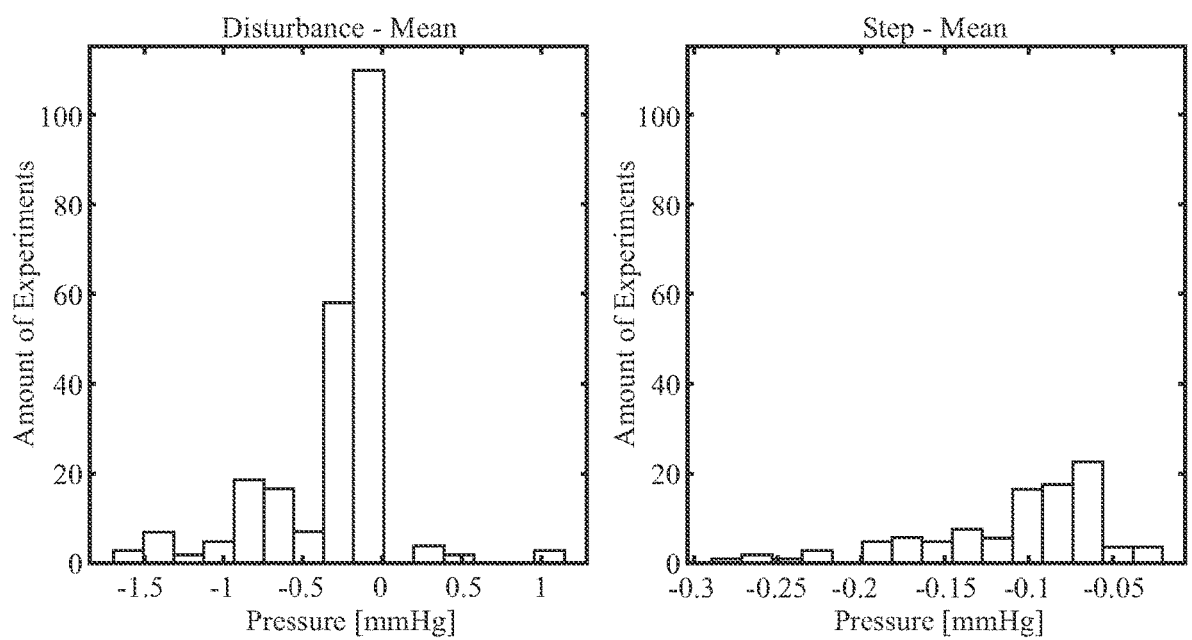
Figure 28:
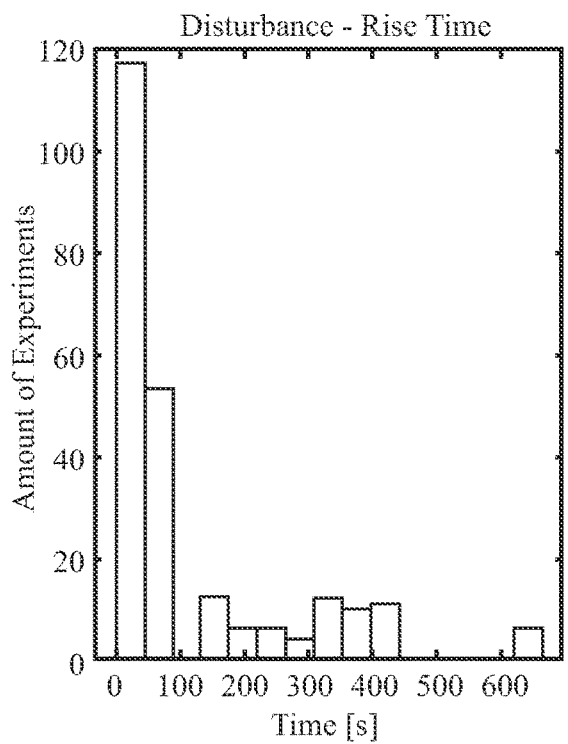
Figure 29:
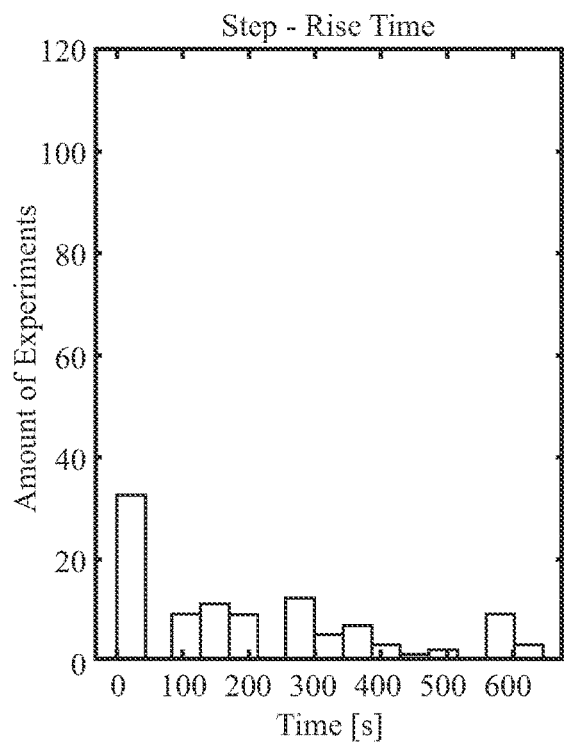
Figure 30:
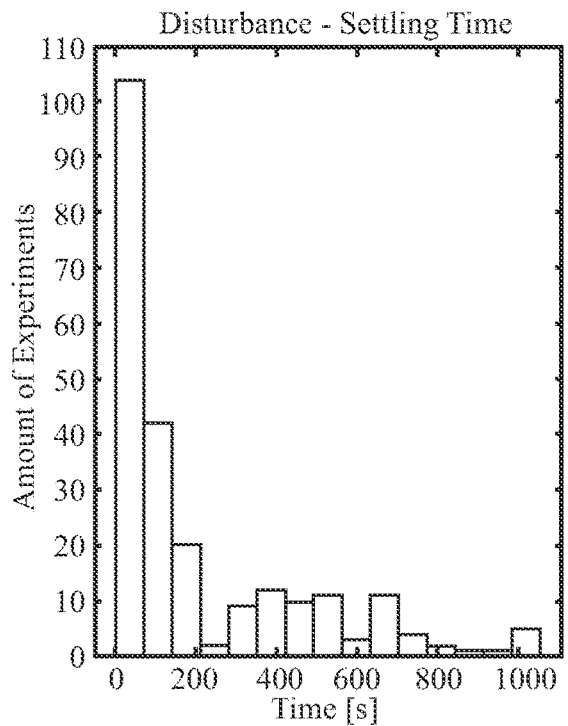
Figure 31:
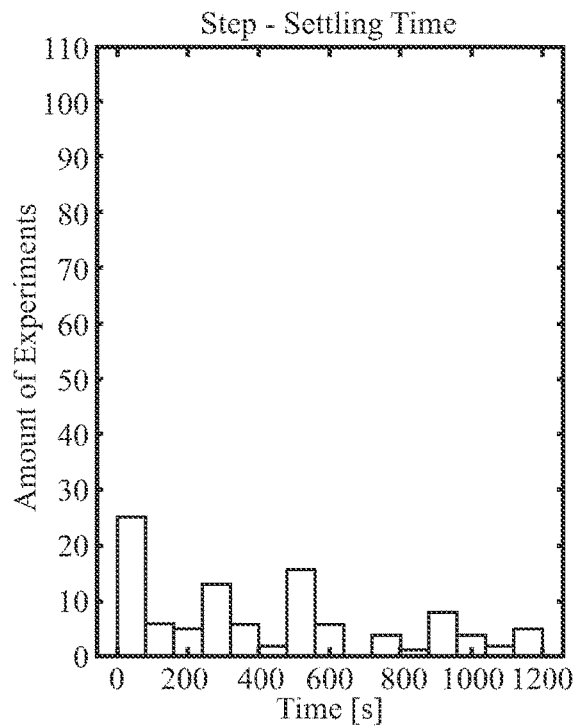

Results overviews are presented in FIGS. 22-31 with comparison in FIG. 22 between the step tests and the disturbance tests in terms of Max mean and Min mean. FIGS. 23 and 24 shows the distribution of the Mean error for the disturbance tests (FIG. 23) and the step tests (FIG. 24). FIG. 25 shows a comparison between the step tests and the disturbance tests in terms of Max variance error and Min variance error. FIGS. 26 and 27 shows the distribution of the Variance error for the disturbance tests (FIG. 26) and the step tests (FIG. 26). FIGS. 28-29 show the distribution of the Rise time in the disturbance tests (FIG. 28) and the step tests (FIG. 29). FIGS. 30-31 show the distribution of the Settling time in the disturbance tests (FIG. 28) and the step tests (FIG. 29).

All in all it can be summarized that:
The step tests mean error was between −0.2881 and −0.0233 mmHg
The variance of the error was between 0.2738 and 0.8218 mmHg
The disturbance tests mean error was between −1.6413 and 1.1752 mmHg
The variance of the error was between 0.1754 and 0.9569 mmHg Preliminary Validation of Performance and Robustness In Vivo In vivo validation can be conducted using land race pigs or Göttingen minipigs. For example, 4-6 healthy animals can be used with the objective to validate safe system performance and robustness using the same flow range and pressure parameters as ex vivo. Catheters for fluid infusion and aspiration can be implanted into the CSF space of the fully sedated animals using MRI guided stereotactic techniques. An intracranial pressure sensor can be implanted in the brain and connected to the control interface along with the flow pump controlling the fluid exchange. A wide range of infusion and aspiration rates can be tested as well as different system implementations in which catheters are inserted at different positions in the cerebrospinal fluid space. System safety and performance can be tested under a wide range of disturbances, such as catheter occlusion, leakage, high intracranial pressure conditions, sudden mass lesions, etc. Tests of sensor and actuator accuracy can be performed. Compliance measures can be tested at different volumes of induced intracranial mass expansion (catheter inflation).

Characterization of CSF Flow During System Activation

In another in vivo experiment, the system's ability to perform controlled perfusion of the subarachnoid space and exchange of CSF can be characterized. For example, 4-6 fully sedated animals can be used with catheters inserted into the lateral ventricles and a system setup as described above. The system can be used to perform repeated wash-in and wash-out of a traceable compound, such as a CT or MRI contrast agent, and perform simultaneous neuroimaging to assess the rate and distribution of fluid exchange in the subarachnoid space. Experiments can be conducted at different flow rates and intracranial pressures for all animals. In order to estimate the kinetics of the CSF exchange process, i.e. time-concentration kinetics, different activations times of the system can be investigated for each setting and use standard regression techniques and statistical measures to characterize the relationship.

Characterization of CSF Flow During System Activation

In the third in vivo experiment an intraventricular and/or subarachnoid hemorrhage can be induced, e.g. in 4-6 fully sedated animals, in order to test the system's ability to clear the blood using CSF lavage. A suitable volume of blood can be injected into the ventricular system using Mill based stereotactic injection techniques. Neuroimaging (CT or MM) can be performed at baseline, following injection and at repeated intervals after injection and initiation of CSF lavage, in order to visualize and estimate the size of the hemorrhage and thereby quantify the ability of the procedure to rapidly remove the blood clot. Standard regression techniques and statistical methods can be used to characterize the kinetics of the blood clearance at different system flow rates. This experiment would particularly challenge the safety features of the system as the risk of tube obstruction is high due to the presence of blood clots. In addition, it would provide preliminary validation of the apparent potential and treatment efficacy of the presently disclosed system.

Clinical Application of the Presently Disclosed Approach

Figure 32:
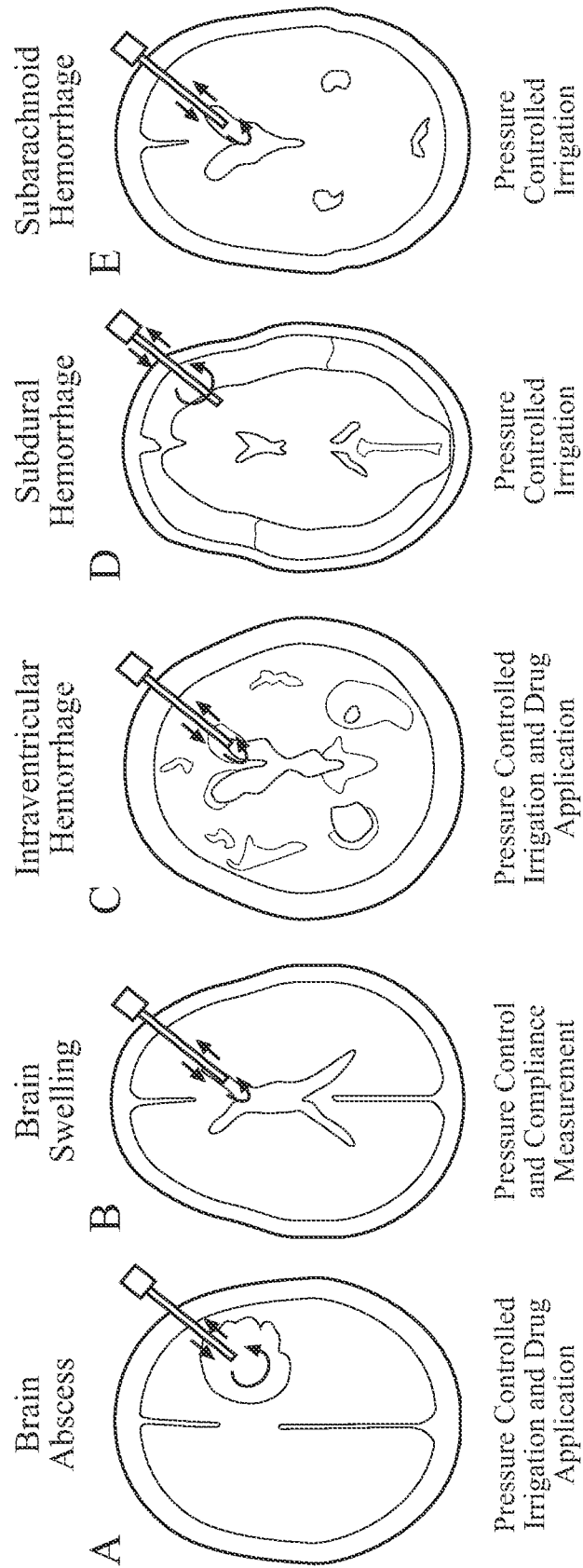
FIG. 32 shows application examples of the presently disclosed approach, with brain abscess in A, brain swelling in B, intraventricular hemorrhage in C, subdural hemorrhage in D and subarachnoid hemorrhage in E.

FIG. 32 shows brain CT scans of five different disease conditions for which the present invention can be applied using different embodiments and settings.

A. Brain abscess: In this embodiment, the presently disclosed approach is used to treat a destructive encapsulated bacterial brain infection. The catheter is inserted into the abscess to provide pressure-controlled wash-out of bacteria, pus and debris, while simultaneously applying antibiotics, which would otherwise not enter the infectious cavity sufficiently, due to the blood-brain-barrier.

B. Traumatic brain injury and brain swelling: In this scenario, the catheter is inserted in the natural fluid cavity of the brain to regulate the fluid volume and maintain a desired intracranial pressure. This is critical to optimize blood perfusion and avoid brain damage.

C. Stroke: Here the patient has acquired a serious brain hemorrhage (bleeding). The catheter is inserted to evacuate the hematoma by flushing out the blood actively, while maintaining a stable pressure. Drugs may be applied to dissolve the blood clot and facilitate the process.

D. Chronic subdural hematoma: This condition occurs following head trauma. Massive blood volumes are present over both brain hemispheres and the brain is extensively compressed by the blood collection. The catheter is inserted to flush out the blood in a controlled and minimally invasive fashion, thereby avoiding high-risk open surgery.

E. Subarachnoid hemorrhage: In this situation the bleeding is distributed throughout the inaccessible fluid space on the surface and base of the brain. The catheter is placed in the ventricular system to flush out the blood and simultaneously maintain a low pressure and estimate compliance. In all scenarios, the technology estimates intracranial compliance to alert the treating physician of potential pressure increase in due time for counteractive surgical or medical treatment. This will help avoid secondary brain damage.

REFERENCES (1) LIU G, ZHAN Y, WU H, YANG X, LI S. Clinical observation of cerebrospinal fluid replacement combined with intrathecal injections in treatment of tuberculous meningitis. Chinese Journal of Nosocomiology 2011; 13:044.

(2) Shaanxi Provincial T, Guoqiang W Y N. In 34 cases of tuberculous meningitis with cerebrospinal fluid replacement and intrathecal injection. Shaanxi Medical Journal 2013; 6:039.

(3) Aydin M D, Gundogdu C, Akcay F, Gursan N. Protective effects of cisternal irrigation on leptomeningeal and cortical structures in meningitis: an experimental study. Neurol India 2005 March; 53(1):90-92.

(4) Hanggi D, Steiger H. The influence of cisternal and ventricular lavage on cerebral vasospasm in patients suffering from subarachnoid hemorrhage: analysis of effectiveness. Early Brain Injury or Cerebral Vasospasm: Springer; 2011. p. 95-98.

(5) de Aguiar, Paulo H Pires, Barros I, Paiva B L, Simm R F. Removal of clots in subarachnoid space could reduce the vasospasm after subarachnoid hemorrhage. Cerebral Vasospasm: Neurovascular Events After Subarachnoid Hemorrhage: Springer; 2013. p. 91-93.

(6) Ding W, Gao N, Li M X, Ding L J, Li F F, Mou L. Clinical evaluation of the efficacy of the combination of aneurysm embolization and cerebrospinal fluid replacement in the treatment of aneurysmal subarachnoid hemorrhage. Eur Rev Med Pharmacol Sci 2015; 19(3):402-405.

(7) McBee N, Kase C, Carhuapoma J R, Jallo J, Aldrich C, Lane K, et al. Mortality Review For The First 400 Patients Enrolled In The Clot Lysis: Evaluation Of Accelerated Resolution Of Intraventricular Hemorrhage Trial (CLEAR III). Stroke 2015; 46 (Suppl 1): A94-A94.

(8) Ali S, Maryam K, Hassan H M. A Proposed Management of Accidental Intrathecal Injection of a Wrong Drug: Spinal Washing. J. Appl. Environ. Biol. Sci 2014; 4(8): 292-295.

(9) Jakobson Â, Kreuger A, Mortimer Ö, Henningsson S, Seidel H, Moe P. Cerebrospinal fluid exchange after intrathecal methotrexate overdose. A report of two cases. Acta Paediatrica 1992; 81(4):359-361.

(10) Makar G, Al-Zubaidi M, Amar S, Feiz-Erfan I, Mehta D. Successful large-volume cerebrospinal fluid aspiration for an accidental overdose of intrathecal cytarabine. Medical Oncology 2013; 30(2):1-3.

The invention claimed is:

1. A bio-liquid replacement system for controlled infusion, effusion, and/or perfusion of a biological liquid or a biocompatible liquid to and from a body cavity of a subject, comprising:
   at least one sensor for continuously measuring at least one parameter associated with the body cavity,
   a pump unit for infusing the biological liquid or the biocompatible liquid into the body cavity and aspirating the biological liquid or the biocompatible liquid out of the body cavity,
   a processing unit configured for continuously 1) calculating at least one physiological parameter based on the at least one measured parameter, and 2) defining at least one target parameter, such that the at least one target parameter is slightly offset from the at least one physiological parameter in a time varying manner, and
   a flow controller configured for controlling said pump unit based on said at least one target parameter such that continuous compensatory changes are induced in a liquid volume in the body cavity,
wherein the processing unit is configured for continuously estimating a compliance within the body cavity based on said at least one calculated physiological parameter; and wherein the compliance is estimated as $$\complement(t) = \frac{\int_{t_s(t)}^{t} \Delta \dot{v}(k) dk}{f_p(t) - f_p(t_s(t))},$$

where $\Delta \dot{v}(k) = \dot{v}_{infusion}(k) - \dot{v}_{aspiration}(k)$ is a net perfusion flow rate at time k in a time interval $[t, t_s(t)]$, $f_p(t)$ is a value of a function, $f$, of a measured pressure, p, at time t, $f_p(t_s(t))$ is a value of the function, $f$, of the measured pressure, p, at time $t_s(t)$.

2. The system according to claim 1, wherein the at least one measured parameter associated with the body cavity is selected from the group consisting of: a temperature, a pressure, an intra-cranial pressure, an oxygen tension, a liquid flow rate, a flow rate of cerebrospinal fluid and/or artificial cerebrospinal fluid, and a concentration of at least one predefined biological compound.

3. The system according to claim 1, wherein a type of the at least one target parameter is selected from the group consisting of: a target pressure, a target infusion flow rate, a target aspiration flow rate, a target liquid exchange flow rate (perfusion flow rate), a target temperature, a target oxygen tension, and a target concentration of a biological compound.

4. The system according to claim 1, wherein the at least one target parameter is a non-physiological time-invariant signal or function, which is a constant signal or function.

5. The system according to claim 1, wherein the at least one target parameter is time varying and wherein time variation of the at least one target parameter is provided by overlaying a target parameter with a non-physiological time-varying signal or function.

6. The system according to claim 5, wherein the non-physiological time varying signal or function is a sine wave or a piecewise constant function (step-function), having a predefined amplitude and period.

7. The system according to claim 1, wherein a time variation of the at least one target parameter is provided by a physiological time-varying signal, which is a time varying physiological signal originating from a heartbeat and/or breathing of the subject.

8. The system according to claim 1, wherein the at least one target parameter is defined externally, by a user of the system.

9. The system according to claim 1, wherein the body cavity is located inside an intracranial space or a spinal canal of a human or an animal.

10. The system according to claim 1, wherein the biological liquid is cerebrospinal fluid and/or modified cerebrospinal fluid, and wherein the biocompatible liquid is artificial cerebrospinal fluid, and/or modified artificial cerebrospinal fluid, a physiological saline solution, and/or a solution containing a medical compound or a drug.

11. The system according to claim 1, wherein the at least one physiological parameter is calculated as a function, $f$, of the at least one measured parameter, which is a moving average, which is an average acquired over a predefined period of at least one digital sampling period, or at least one millisecond, or at least 1 second, or at least 3 seconds, or at least 5 seconds, or at least 10 seconds, or at least 20 seconds.

12. The system according to claim 1, wherein the compliance is defined as dV/dP, where V is volume and P is pressure, and d defines a differential operator or a difference operator of a variable over time.

13. The system according to claim 1, wherein $t_s$ is defined as:

$$t_s(t) = \begin{cases} t, & \text{if sign}(\Delta \dot{v}(t)) \neq \text{sign}(\Delta \dot{v}(t - \delta t)) \\ t - T_{limit}, & \text{if sign}(\Delta \dot{v}(t)) = \text{sign}(\Delta \dot{v}(t - \delta t)) \text{ and } t - t_s(t - \delta t) \geq T_{limit} \\ t_s(t - \delta t), & \text{if sign}(\Delta \dot{v}(t)) = \text{sign}(\Delta \dot{v}(t - \delta t)) \text{ and } t - t_s(t - \delta t) < T_{limit} \end{cases}$$

where $T_{limit}$ is a predefined period of time and $\delta t$ is an infinitesimally small period of time.

14. The system according to claim 13, wherein $t_s(t)$ is discretised as $$i_s[i] = \begin{cases} i, & \text{if sign}(\Delta \dot{v}[i]) \neq \text{sign}(\Delta \dot{v}[i - 1]) \\ i - \dfrac{T_{limit}}{T_{sample}}, & \begin{array}{l} \textit{if } \text{sign}(\Delta \dot{v}[i]) = \text{sign}(\Delta \dot{v}[i - 1]) \text{ and} \\ i - i_s[i - 1] \geq \dfrac{T_{limit}}{T_{sample}} \end{array} \\ i_s[i - 1], & \begin{array}{l} \text{if sign}(\Delta \dot{v}[i]) = \text{sign}(\Delta \dot{v}[i - 1]) \text{ and} \\ i - i_s[i - 1] < \dfrac{T_{limit}}{T_{sample}} \end{array} \end{cases}$$

where $T_{sample}$ is a sampling time and $T_{limit}$ is a predefined period of time.

15. The system according to claim 1, wherein outliers are removed in the estimation of the compliance.

16. The system according to claim 1, wherein the at least one measured parameter and the estimation of the compliance are used to produce an estimate of a body cavity pressure-volume relationship, wherein the measured pressure and an inverse of the estimated estimation of the compliance at corresponding time-points are used to represent an independent variable and a slope of an intracranial pressure-volume relationship at a given time-point, respectively.

17. The system according to claim 1, wherein the at least one measured parameter and the estimation of the compliance are used to produce an estimate of a body cavity reserve-volume capacity, wherein the estimation of the compliance and an estimated intracranial pressure-volume relationship is used to estimate a change in an intracranial volume, such that an intracranial pressure attaining a given value is obtained.

18. The system according to claim 1, wherein the at least one sensor is an implantable sensor.

19. The system according to claim 1, wherein the at least one sensor is a non-invasive sensor.

20. The system according to claim 1, wherein the at least one sensor comprises at least one flow sensor for measuring an infusion rate, an effusion rate and/or a perfusion rate.

21. The system according to claim 1, wherein the system is configured for using multiple access pathways to the body cavity to perform said infusion, said effusion, or said perfusion continuously or sequentially.

22. The system according to claim 1, further comprising at least one access pathway to the body cavity, and wherein the system is configured for changing a direction of flow of the infusion and/or the effusion and/or the perfusion in each of the at least one access pathway to allow for directional flow changes and prevention of access pathway obstruction.

23. The system according to claim 1, wherein volume changes of the body cavity induced by the system represent an estimate of a physiological volume-change caused by a heartbeat of the subject.

24. A bio-liquid replacement system for controlled infusion, effusion, and/or perfusion of a biological liquid or a biocompatible liquid to and from a body cavity of a subject, comprising:
   at least one sensor for continuously measuring at least one parameter associated with the body cavity,
   a pump unit for infusing the biological liquid or the biocompatible liquid into the body cavity and aspirating the biological liquid or the biocompatible liquid out of the body cavity,
   a processing unit configured for continuously 1) calculating at least one physiological parameter based on the at least one measured parameter, and 2) defining at least one target parameter, such that the at least one target parameter is slightly offset from the at least one physiological parameter in a time varying manner, and
   a flow controller configured for controlling said pump unit based on said at least one target parameter such that continuous compensatory changes are induced in a liquid volume in the body cavity,
   wherein the processing unit is configured for continuously estimating a compliance within the body cavity based on said at least one physiological parameter; and
   wherein the estimation of the compliance is filtered in accordance with $$\hat{c}(l) = \begin{cases} \alpha \cdot \hat{c}_{raw}(t) + (1-\alpha) \cdot \hat{c}_{raw}(t-1), \\ \text{if } \hat{c}_{raw}(t) > 0 \text{ and } \text{var}(\hat{c}_{raw}(t_s, \ldots, t)) < VarLimit \\ \hat{c}(t-1), \text{ otherwise} \end{cases}$$

where var is a variance operator and VarLimit is a predefined variance limit.

25. A method for estimating compliance within a body cavity of a subject based on controlled infusion, effusion, and/or perfusion of a biological liquid or a biocompatible liquid to and from the body cavity, the method comprising the steps of:
   continuously obtaining at least one physiological parameter associated with the body cavity,
   continuously defining at least one target parameter associated with the body cavity, such that the at least one target parameter is slightly offset from the at least one physiological parameter, in a time varying manner, such that continuous compensatory changes are induced in a liquid volume in the body cavity, and
   continuously estimating the compliance within the body cavity based on said at least one physiological parameter;
wherein the compliance is estimated as $$\hat{c}(t) = \frac{\int_{t_s(t)}^{t} \Delta \dot{v}(k) dk}{f_p(t) - f_p(t_s(t))},$$

where $\Delta \dot{v}(k) = \dot{v}_{infusion}(k) - \dot{v}_{aspiration}(k)$ is a net perfusion flow rate at time k in a time interval [t, $t_s(t)$], $f_p(t)$ is a value of a function, $f$, of a measured pressure, p, at time t, $f_p(t_s(t))$ is a value of the function, $f$, of the measured pressure, p, at time $t_s(t)$.

26. A compliance estimator system for estimating compliance within a body cavity, comprising:
   a communication unit for receiving data corresponding to at least one measured parameter related to the body cavity and for communicating with a flow controller, and
   a processor configured for:
      a) calculating at least one physiological parameter based on the at least one measured parameter,
      b) defining at least one target parameter, such that the at least one target parameter is slightly offset from the at least one physiological parameter in a time varying manner, and
      c) forwarding a control signal, based on the at least one target parameter, to the flow controller, such that continuous compensatory changes are induced in a liquid volume in the body cavity,
      d) repeating steps a)-c)
         wherein the compliance within the body cavity is continuously estimated based on said at least one physiological parameter; and
      wherein the compliance is estimated as $$\hat{c}(t) = \frac{\int_{t_s(t)}^{t} \Delta \dot{v}(k) dk}{f_p(t) - f_p(t_s(t))},$$

where $\Delta \dot{v}(k) = \dot{v}_{infusion}(k) - \dot{v}_{aspiration}(k)$ is a net perfusion flow rate at time k in a time interval [t, $t_s(t)$], $f_p(t)$ is a value of a function, $f$, of a measured pressure, p, at time t, $f_p(t_s(t))$ is a value of the function, $f$, of the measured pressure, p, at time $t_s(t)$.

* * * * *